United States Patent [19]

Kass

[11] Patent Number: 4,581,223
[45] Date of Patent: Apr. 8, 1986

[54] INDIVIDUAL LEUKOCYTE DETERMINATION BY MEANS OF DIFFERENTIAL METACHROMATIC DYE SORPTION

[76] Inventor: Lawrence Kass, 1939 Ridge Rd., Hinckley, Ohio 44233

[21] Appl. No.: 129,680

[22] Filed: Mar. 12, 1980

[51] Int. Cl.$^4$ .................. G01N 1/30; G01N 33/49; G01N 33/52
[52] U.S. Cl. ........................................ 424/3; 424/7.1
[58] Field of Search ............... 424/3, 7.1; 8/644, 657; 750/461.2

[56] References Cited

U.S. PATENT DOCUMENTS

| | | | |
|---|---|---|---|
| 2,126,852 | 8/1938 | Wolff. | |
| 3,560,135 | 2/1971 | Yamayo | 8/657 |
| 3,617,185 | 11/1971 | Drautz | 8/657 |
| 3,916,205 | 10/1975 | Kleinerman | 250/302 |
| 3,961,039 | 6/1976 | Sternheimer | 424/3 |
| 3,985,500 | 10/1976 | Steck | 8/657 |
| 4,146,604 | 3/1979 | Kleinerman | 424/3 |
| 4,400,370 | 8/1983 | Kass | 8/657 |

FOREIGN PATENT DOCUMENTS

| | | |
|---|---|---|
| 0004061 | 9/1979 | European Pat. Off. . |
| 1331568 | 9/1973 | United Kingdom . |
| 1400897 | 7/1975 | United Kingdom . |
| 1473945 | 5/1977 | United Kingdom . |
| 1480576 | 7/1977 | United Kingdom . |

OTHER PUBLICATIONS

Gurr, Synthetic Dyes in Biol. Med. & Chem., Acd. Press, NY, 1971, pp. 54, 55, 90, 117, 147–149, 395, 805.
Conn's, Biological Stains, Williams & Wilkins, Baltimore, 9th Ed., 1977, pp. 43, 368, 404–407, 415–429.
Gray, The Ency. of Microscop. & Microtech., Van Nostrand–Reinhold Co., NY, 1973, pp. 398–399, 469, 551, 563.
Humason, Animal Tissue Tech., W. H. Freeman & Co., San Francisco, 1972, pp. 128–132.
Ruddell, Chem. Abs., vol. 89, 1978, Ab. No. 89:54252q; Chem. Sub. Index, p. 2791CS.
Simpson, Stain Tech., vol. 45, No. 5, 1970, pp. 221–223.
MacConaill, Ireland J. Med. Sci., Jun. 1964, pp. 243–250.
Sabin, Bull. Johns Hopkins U., vol. XXXIV, No. 391, Sep. 1923, pp. 277–288.
Spiridonovitch, The Anatomical Record, vol. 27, Jan.–May 1924, pp. 367–373.
Moore, PSEBM, vol. 82, 1953, pp. 601–603.
Hallberg, Acta Med. Scand. Suppl., vol. 180, 1946, pp. 7–15.
Pilot, Use of Base Fluids for Counting Eosinophils, U. of Ill., May 23, 1950, pp. 870–871.
Williams, The J. of Lab. & Clin. Med., vol. VIII, Oct. 1922–Sep. 1923, pp. 250–253.

Primary Examiner—Christine M. Nucker
Attorney, Agent, or Firm—Richard G. Smith

[57] ABSTRACT

Lengthy cytochemical procedures for differentiation, identification, enumeration and diagnostic study of leukocytes in human blood have been advanced and shortened by a rapid method of optical differentiation of the five individual white blood cell species by selective use of basic quaternary metachromatic dye staining of supravital blood at controlled temperature. Presently a manual method, the improvement provides essential groundwork for improved accuracy in automated differential leukocyte counting.

16 Claims, 11 Drawing Figures

INDIVIDUAL LEUKOCYTE DETERMINATION BY MEANS OF DIFFERENTIAL METACHROMATIC DYE SORPTION

BACKGROUND OF THE INVENTION

1. Field of the Invention

The present invention relates to an improvement in the field of cytology and more particularly a microscopic method of supravital blood analysis by which under normal white light illumination of a microscopic field optical differentiation, identification, comparisons and ennumeration of each of the five white blood cells is made possible by use of a single pure dye without fixation and more accurately and rapidly than heretofore by manual or automated differential leukocyte counters.

2. Description of the Prior Art

Ehrlich made biological elements more readily and easily recognized under microscopic examination and for photographic observation by use of dye stains (aniline dyes) to identify certain white blood cells. Ehrlich was the first to note that some dyes were metachromatic, observing that the staining of the cell causes the cell to take on a color different than that of the stain or expected color from the stain. Basophils, for example, were observed to take on a color different from the stain. Other histological specimens other than blood cells have also been reported to stain in a plurality of identifiably different colors.

A review of the state of the art indicates it is almost universal practice, before staining (which ordinarily uses a plurality of chemically differing dyestuffs in admixture) to employ a fixative procedure which may require up to an half hour treatment before the biological specimen is subjected to dye stain. Fixatives are generally preservatives and denaturants that often interfere with the sensitivity of the dye sorption. Illustratively, fixatives include formaldehyde both as liquid and vapor, absolute alcohols (methyl), picroformal, etc. Very often living cells do not stain using vital dyes and fixatives have been essential to staining the specimens. Cytochemistry includes considerable information on techniques developed to assure reproducible staining of blood cells. Many essential additives are normally unstable and deteriorate rapidly, thus making cellular identification difficult and in some instances unreliable. Dr. Thomas E. Necheles has observed in relation to leukocyte analysis That this "system has undergone little or no change in fifty years".

Dye staining does serve, however, as a means of discernment of otherwise undiscernable detail of conferring a color reaction on cells and their stainable components; metabolic, functional or pathological.

United States hospitals began leukocyte counting in the early 1900's, using the count as indicia as to whether emergency surgery was necessary, for example. In the U.S. alone, more than half a million differential counts are performed every day, most of them by manual methods. It is important that total white cell counts and differential cell counts be performed and reported without delay. Time is of essence and providing required analysis more rapidly is a desideratum.

The value of leukocyte counting having been established, the demand for rapid blood analysis has developed so that beginning about 1950 with the work of Mellors and Papaincolaou (1952) development of automated differential leukocyte counting instrumentation means had developed into a plurality of instruments by 1980. The "CYDAK" unit was early used to investigate the feasability of blood cell classification which pointed up the importance of specialized staining procedures and features were extracted from optical density histograms of each cell image. The procedure established that cells could be differentiated into four of the five classes of leukocytes, namely; neutrophils, eosinophils, lymphocytes and monocytes. Young (1969) published results on an automated classification of five cell classes and Bacus in 1971 extended the differentiation.

However, it is understood that automated differential systems presently rely upon multiple dye usage and dye degradation systems or indirect fluorescent measurement using fluorescent dyes. The latter are described by Kleineman in U.S. Pat. Nos. 3,916,205 and 4,146,604 which disclosure is included herein by reference and indicates the present state of the art in some measure. Here again it will be noted that fixatives were employed as is standard practice in the method of the patentee.

In the prior art staining of blood it has been observed that it is practice to use two or more stains in combination (Romanowski, Giemsa and Wright stains). These methods are difficult in practice to provide quality control. The methods require standardization in preparation of each dye stain component as well as in the method of specimen staining. In development of successful automated leukocyte counters, reproducibility of staining is even more important to verifiable analysis.

"LARC" stainer (used in commercial automated differential leukocyte counter) is reported (Mogler 1973) to be a mixture of some ten thiazine dyes, eosin Y and $2^1, 4^1, 5^1$ tribromofluorescein (P. N. Marshall). Present art stains most often are in fixative alcoholic solutions and employ two or more stains in combination. Accurate analysis of vital blood staining is made most difficult. With the difficulty presented in the controlled oxidation of methylene blue essential to Romanowski stains, for example, the problems of quality control of the added ten individually different dye stains as are used in combination become awesome.

It has been recognized in the art that the wide-spread standardization and adoption of a limited number of stains would ensure greater accuracy and reproducibility in cytological studies. Serious introduction of artifacts have been observed by use of fixatives and cause difficulty in interpretation and misinterpretation in leukocyte differentiation and ennumeration. pH adjustments, heavy metal cations have been reported to prevent cytochemical tests from working in the expected manner. Some dyes, particularly azo dyes, are noted to demonstrate non-specific precipitation around cells; other degenerative changes in fixed blood samples include vacuoles, clover-leafing of nuclei, distortion cell shapes and smudges and interference with ideal staining. The importance of performing differential counts on as near living cells in the shortest possible time in order to obtain optimally useful and valuable blood cell analyses has been recognized. Alcoholic dye solutions interfere with supravital staining. So far as is known, freshly prepared water soluble stains exhibit a minimum denaturant effect upon supravital blood during examination. All dyestuffs are more or less toxic to the blood cells, but some are more so than others. It is material that the cells under examination remain living as long as possible. Rapidity of staining obviously shortens the exposure time, thus allowing greater opportunity to examine leukocyte cells before all vitality is lost. Automated differential leukocyte counting in less minutes is sought for.

Studies and review of the prior art of performing microscopic blood analyses and disease diagnosis has indicated it is not unusual for pathologists to warm the dye and the blood speciment to body temperatures (about 37° C.) before contact. Dr. Sabin had a "warm box" to insure temperature control.

It has also been noted that some dyes used in the prior art are quite temperature sensitive. The literature reports that cresylecht violet is not an operative stain above 30° C. and the most favorable temperature for neutral red is about 32° C. Neutral red gives no appreciable differential color staining. It is considered important for the purposes of this method as disclosed herein that the dyestuff be useful to stain leukocytes at temperatures as high as 37° and no difficulty has been observed with the select dyes to temperatures of about 40° C.

This invention has been found to be limited to basic cationic dyestuffs, and that they are as a class, relatively few in number in comparison to all the many classification of known dyestuffs. The Colour Index for (1956-63) lists some 3000 synthetic organic dyestuffs. Of these only 190 are cationic. Out of one relatively extensive available catalog listing of basic cationic dyes there were sixty-one listed species tested in the present inventive use. Of the total tested, three were found useful for the purposes and within purview of this invention. In another survey of eighteen basic quaternary dyes in a listed public dye offering, only one was found to stain one species of leukocyte metachromatically.

Insofar as is known, the prior art fails to disclose basic cationic quaternary dyestuffs effective to selectively stain species of leukocytes, to be effective metachromatically and at temperatures of 37° C.–40° C. The prior art discloses no specific dyes used to distinguish monocytes instantly from others of the leukocyte species. The prior art discloses no simple method for identification and counting of lymphocytes.

BRIEF DESCRIPTION OF THE DRAWINGS

Six Plates of Spectral Curves identified as FIGS. 1 through 11, identify the Spectral Curves originally prepared by direct instrument recorded measurement and redrafted from the originals in accordance with the foregoing Plates. These Plates and Curves are a record part hereof.

SUMMARY OF THE INVENTION

Figure 1:
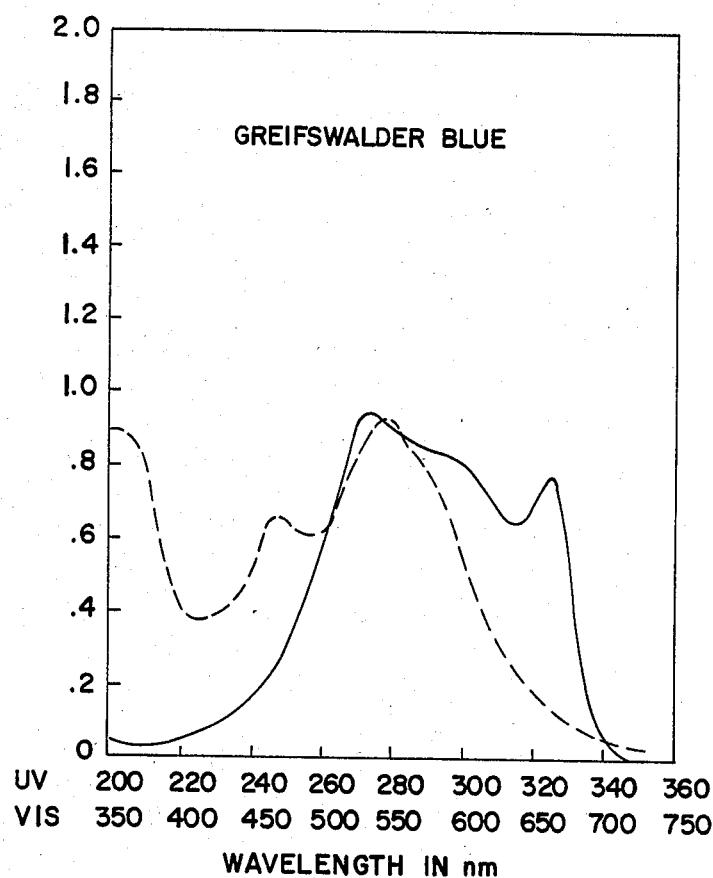
Figure 2:
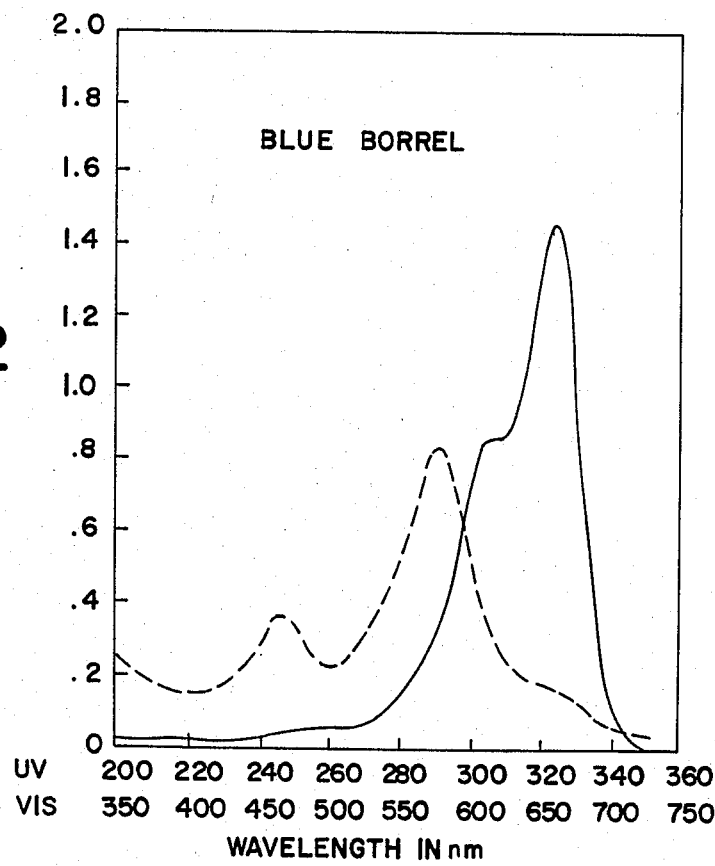
Figure 3:
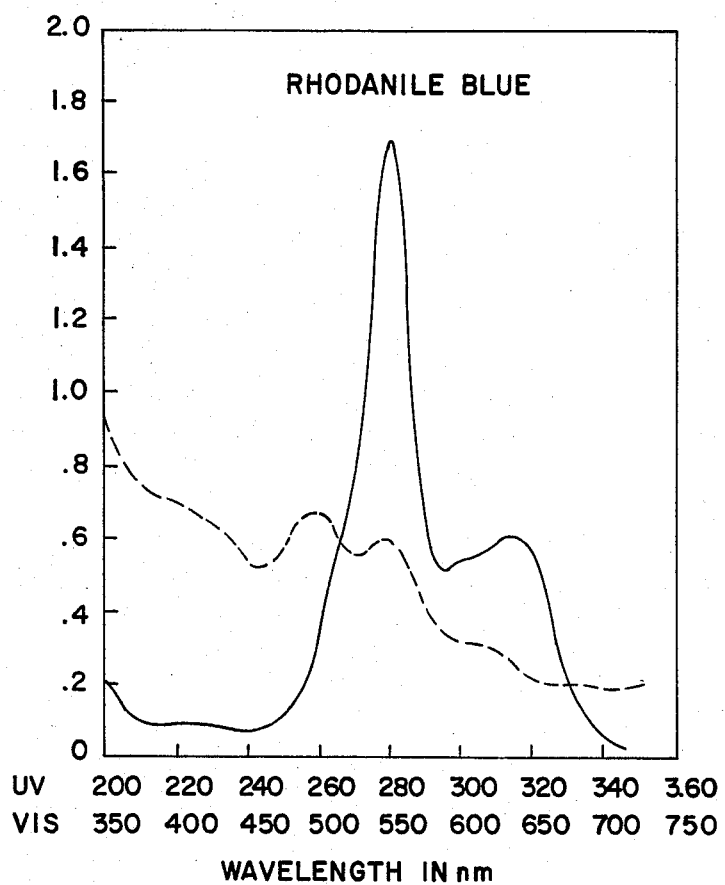
Figure 4:
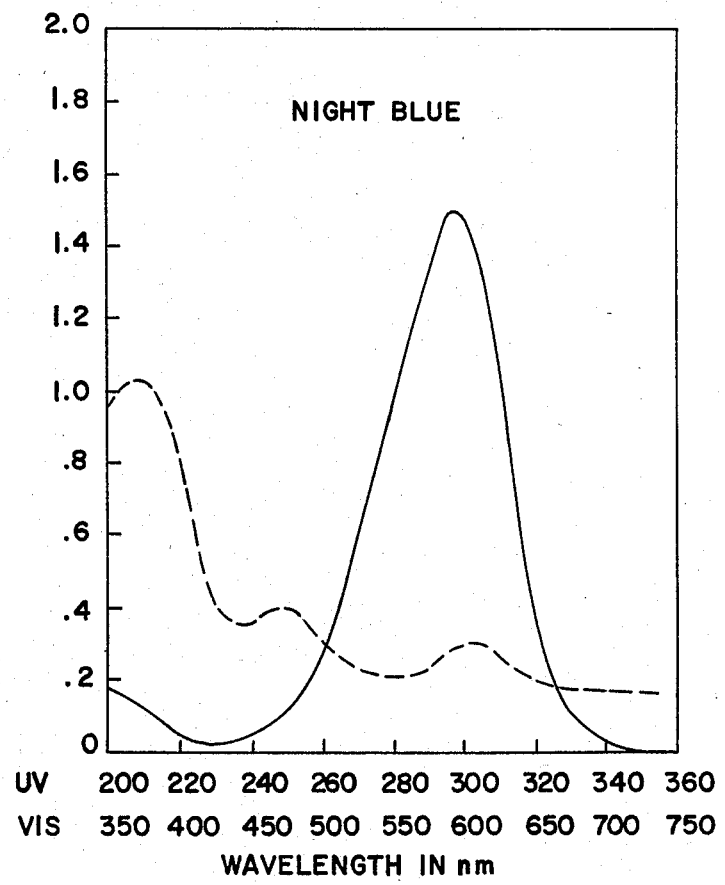
Figure 5:
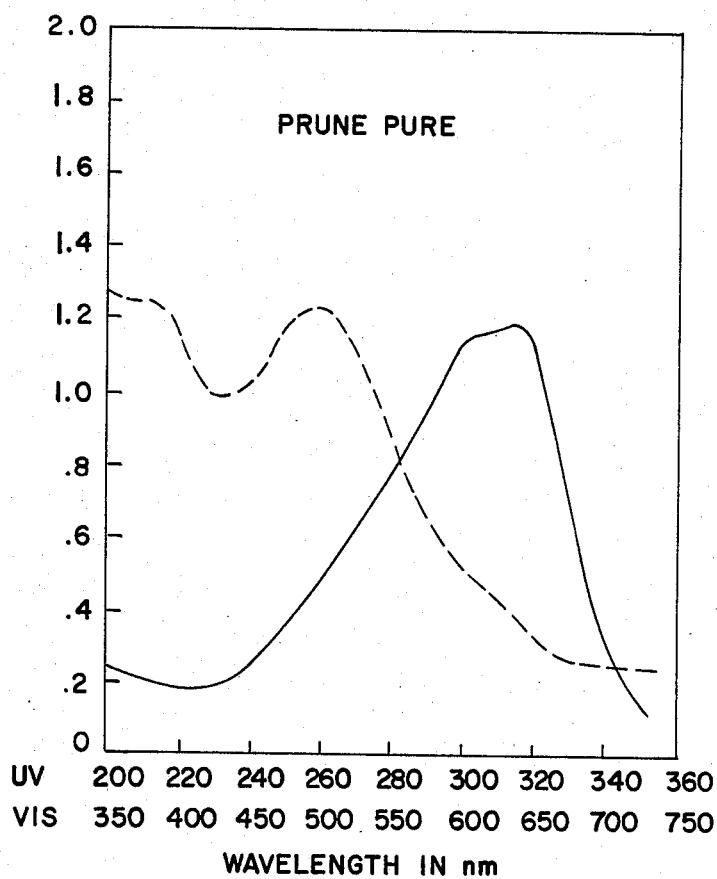
Figure 6:
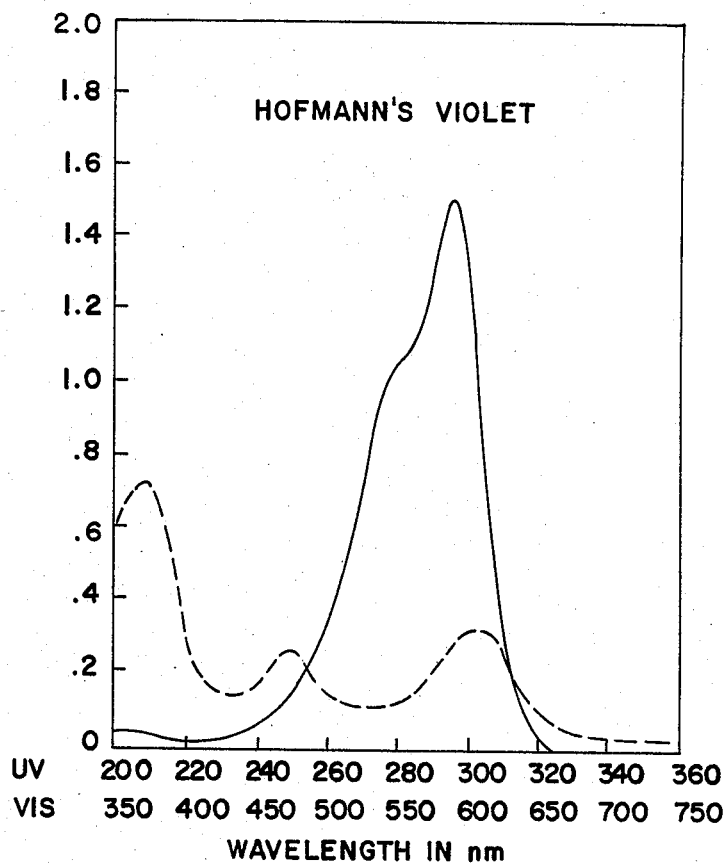
Figure 7:
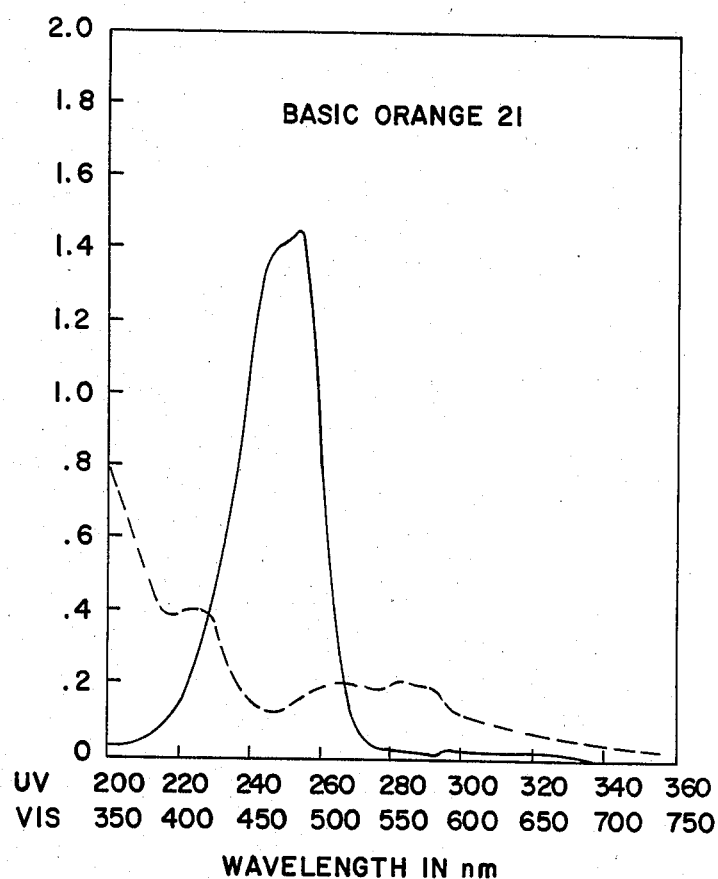
Figure 8:
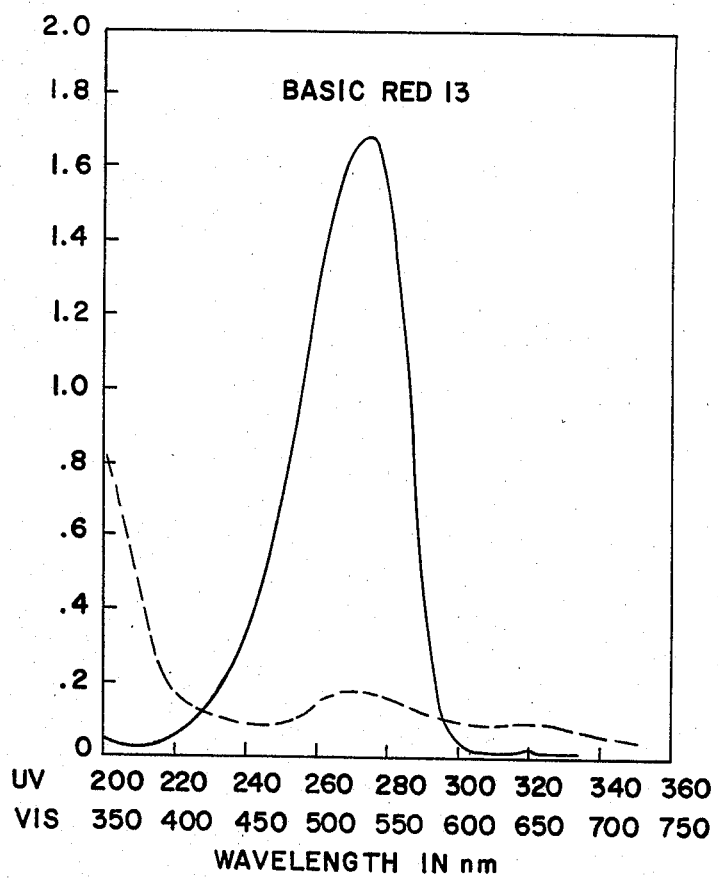
Figure 9:
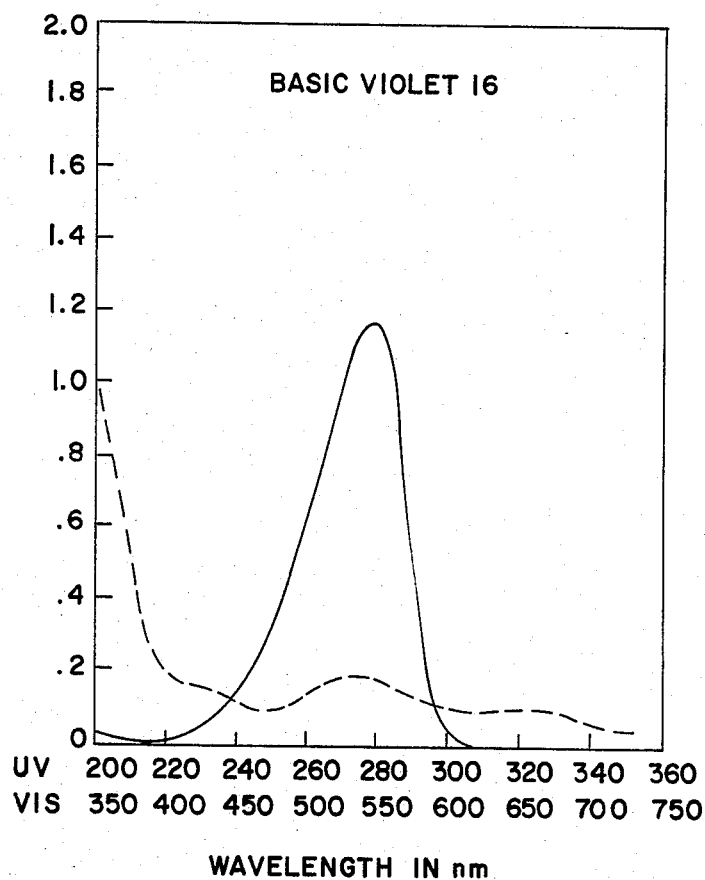
Figure 10:
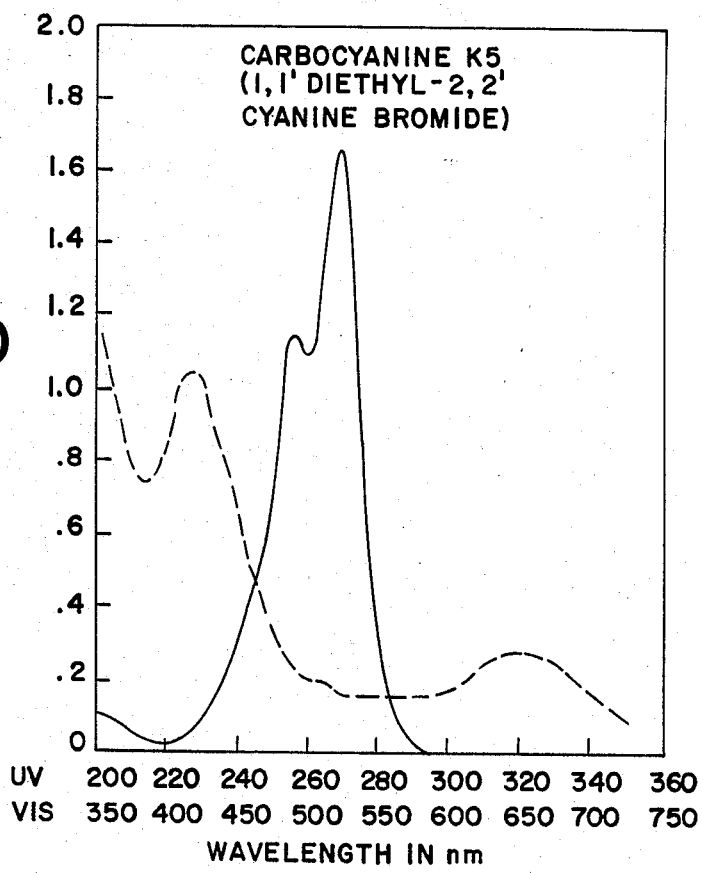
Figure 11:
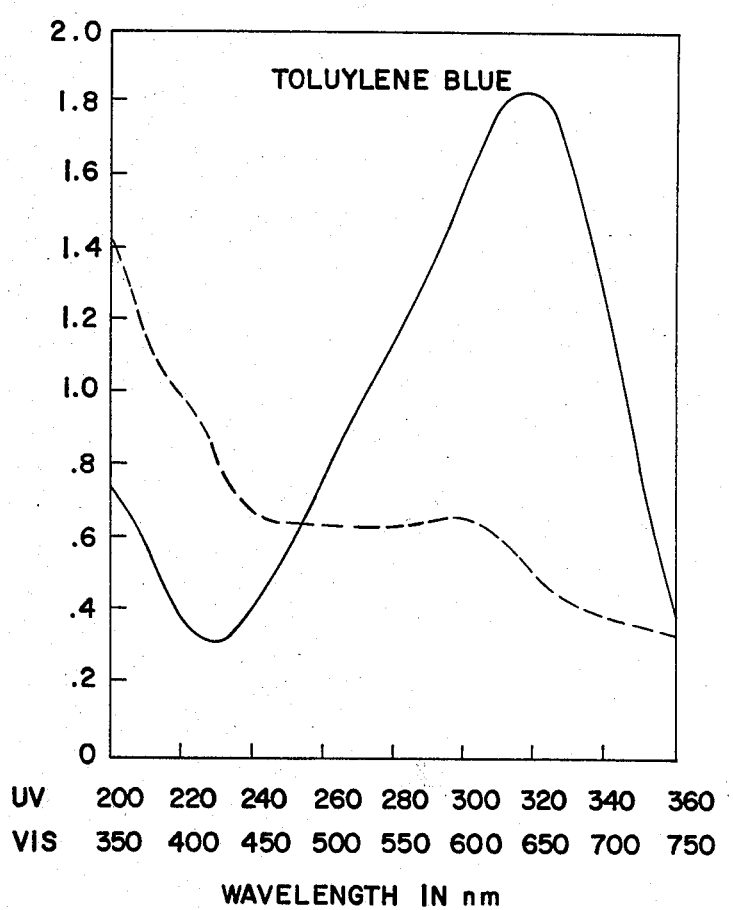

The present invention advances the art of cytology by providing a series of less than a dozen basic quaternary cationic organic dyestuffs which are selectively sorbed by one or more peripheral blood cell leukocytes which provides unusual improvement in identification and differentiation between members of the species of the white blood cells. The peripheral blood cell leukocyte species include: polymorphonuclear leukocytes or neutrophils, eosinophils, basophils, lymphocytes and monocytes. Heretofore, cytomchemical means and complex stains had to be used for differentiation, often requiring an hour or more of tedious preparation to prepare and microscopically analyze a single species.

In practice of the present invention it now becomes possible to differentially stain and identify with one single pure dye in a simple aqueous contact with a pheripheral venous blood sample without fixatives at body temperature, or a leukocyte enriched specimen thereof, each one of the five species or types of white blood cells as listed. This identification occurs very promptly, without careful cytochemistry or complex preparation.

Each of the leukocyte species, by sorbing or failing to sorb the dyestuff in some instances, becomes differentiated by reflecting an image having spectrally identifiably different colors, sorbing other colors within the normal light spectrum including primarily the visible light range but not excluding the infra red or ultra violet ranges which are important to automatic equipment not limited by the human eye response. There is no need to rely or depend upon fluorescent dye response.

Thus, each individual species can be differentiated from its neighbors, each species can be counted, the total leukocyte count determined, each species can be studied as to its morphology, and many determinations made of great value to the health sciences.

Fundamentally, each of the above named leukocytes differentially sorb light from the same pure dyestuff, depending upon the quality of the dye and the species of leukocyte stained.

In the absence of fixatives, a basic dye is sorbed metachromatically so that each one class, type or species of leukocyte reflects a characteristic light spectra or color different from every other class, type or species of leukocyte present in the sample. Metachromasia of the eight principal dyestuffs of this invention is believed to be most unique. The first four dyestuffs listed in Table I stain each and every class, type or species of leukocyte so that it reflects an identifiably different spectral color. These dyes, each one alone, make possible practice of the invention. The second four dyes listed in Table I metachromatically stain all of the class, types or species of leukocytes except the lymphocytes. Each species so sorbs the metachromatic stain as to reflect a distinguishing light spectra or color in the visible light range. Combinations of the dyes of this invention may be useful in some leukocyte analyses.

The primary standard for identification of this novel class of dyes is their spectral curves should absolute identification be raised in issue.

Each dye is identified by a standard name, where the name is known, and an assigned name where not known. A secondary standard for identification is a standard Color Index Number or a Michrome number where such is known. In the examples and descriptive disclosure which follows, chemical structural formulas where known are sometimes used to identify the useful dyestuffs of this invention.

In only one case, the useful dye is of such obscure nature that nothing has been found to illuminate its history, chemistry or use. This obscure dye is known as Greifswalder's blue. In a second case, an obscure reference found after extensive search indicated the dye there referred to as Borrels' blue (our blue borrel) is derived directly from methylene blue. The procedure is of record below. From the information on manufacture and the structure of methylene blue the probable dye structure general chemical class definition is found to encompass the blue borrel.

Classification language used herein to identify the unique dyestuffs operative for the purposes herein, namely: basic quaternary metachromatic cationic organic dye encompasses all of the known pure dyes listed in the Tables I, II and III and found useful for the purposes of this invention. All the known composition dyes are structurally related and within the scope of the above language classification. The trio of dyes in Table II are metachromatic in the limited sense as used by Ehrlich but are also very unusual that they are specific only to monocytes. Only monocytes are stained under aqueous contact with these dyes. Their use is alone or in conjunction with the dyes of Table I.

The definitive language "supravital" as used herein is a relatively important limitation. It is applied to the original blood sample and is applied to living cells freshly removed from a living organism, or one freshly sacrificed, or equivalent. As the term is used here it is intended to exclude all "fixatives" but permits use of anticoagulants (heparin, E.D.T.A., etc.). The blood cells may also be removed from bone marrow, urine and other biological specimens containing them.

In all instances, microscopic observations are intended to include white light illumination which is standardly used in clinical microscopy. Automated differential leukocyte counting is presently made possible with normal white light illumination, but so far as is known, no present commercial equipment is directly useful here. This invention in method makes feasible and overcomes many of the problems delaying successful development of computer related automatic differential leukocyte counting means.

The unique dyes used for the purposes of this invention are used in filtered aqueous solution at approximately 1% concentration of the pure dye. The dye concentration is not particularly critical but permits variation. It is preferred that aqueous solutions be used while fresh and that toxic additives not be included. Interference with the metachromatic reaction between dyestuff and the specific type or class of leukocyte may be totally inhibited by the use of classical fixatives.

The term metachromatic believed first used by Ehrlich to describe a stain which changes apparent color when sorbed by certain cells. The dye is said to exhibit metachromosia and has been observed as a property of relatively few pure dyes, chiefly basic dyes which color tissue elements in a different color. Metachromasia is also defined as the assumption of different color spectra by different substances when stained by the same dye. In cytology, as here, metachromatic granules are those which assume a color different from that of the dye used to stain them.

Inherent in the above discussion of the terms metachromatic and metachromasia, two factors are involved. One is the biological cell (and its specialized parts), which has been called "metachromatic" or "chromotropic" and is a quality or character of the biological cell specimen, and the other is the quality of the dye. Very few dyes possess whatever quality is essential to stimulate structure(s) within a cell to exhibit metachromasia. Conn (9th Edition) reports "pure dyes showing this reaction are few in number". Few reports found indicate that the phenomena involves more than two distinct color spectra. In one instance "a light green-blue nuclear stain with a violet metachromasia for cartilage" was reported. However, with stains being normally applied to fixed tissues whose chemical and physical nature is altered by the usual prestaining preparatory procedures, essential cooperation between the character of the natural biological structures within a cell specimen (may be thereby altered and rendered not sensitive to what might otherwise react) so that dye sorption does not occur.

The fact that only a few dyes are "metachromatic" and act metachromatically with different parts of the cell explains the odds against discovery of the surprisingly effective cooperation as disclosed herein between leukocytes and the dyestuffs of this invention.

The broad class of basic dyes which embraces the metachromatic dyes of this invention comprise those in which the auxochrome group is a primary, secondary or tertiary amine group; one nitrogen at least functioning as a quaternary nitrogen atom and upon addition of a colorless anion, most often a halogen acid, can form a salt. As the halogen acids are relatively strong as compared with the immonium base, they are most often mildly acid in reaction, or exhibit an acid pH. The organic chromophoric group is a cation, carrying a positive charge and the halogen ion provides the anion or negative charge.

The novelty and utility of the herein disclosed method resides in a number of concepts. For the first time one can readily, easily and promptly stain all of the peripheral white blood cells or leukocytes in a living cell specimen using essentially only one pure dyestuff. One method, illustratively, provides for the identification, differentiation and study of lymphocytes exclusively by using one dyestuff, blue borrel, at a temperature of about 21°–25° C. The same dye when used at normal blood temperature (37° C.) differentially and metachromatically stains and identifies each and every species of leukocyte by a different spectrally reflected color. Leukocytes accepting a selected dye are stained metachromatically.

Monocytes, heretofore identified by complex cytochemical procedures requiring a tedious hour of careful cytochemistry can be identified and studied for diagnostic purposes instantly with selected single pure dyestuff of this invention.

The general practice of this invention is illustrated by the following:

A 1% solution in distilled water is made up of the selected basic quaternary cationic dye. If practice indicates it necessary, one or more of the subject dyes can be blended together as solutions.

If monocytes only are of concern, a basic quaternary cationic dyes selected from the class consisting of the methine and polymethine dyes specifically, carbocyanine $K_5$ (Spectral Curve 10), basic red 13 (Spectral Curve 9) and basic violet 16 (Spectral Curve 8).

If, however, the specific leukocyte of interest are lymphocytes, then under controlled temperature of 20°–25° C. blue borrel is specific to solely lymphocyte study, and holding the temperature of the dye and the temperature of the supravital blood sample at below blood temperature will, quite surprisingly, selectively stain only the lymphocytes. It has been found that this dyestuff will not stain leukocytes other than lymphocytes within this lower temperature range. However, with slight increase to blood temperature or body temperature (37°–40° C.) blue borrel as a single pure dye provides spectral metachromatic definition and differentiation of all five leukocytes!.

A fresh sample of whole blood (without fixatives being used) anticoagulated with known agents, illustratively heparin, E.D.T.A. or citrate, from which erythrocytes are removed by centifugation, hyptonic lysis, density gradient sedimentation and other like methods or a sample of plasma enriched with leukocytes (or white blood cells) by one of several physico-chemical techniques as suggested above is prepared for further use.

The aqueous solution of the selected single pure dye, or the combination of one or more of the pure dyes as are disclosed in Tables I and II (as illustrated in Table III) are blended to produce a simple aqueous dye solution. (Consideration of various volumetric proportions of the aqueous dye solution, and various strengths of aqueous dye solutions may provide optimum conditions for various specific cytological analyses.) Further experimentation may lead to specific combinations having particular advantage and is contemplated by but beyond the scope of this disclosure.

Blood samples may be made available from various sources but fresh samples of venous blood from which erythrocytes have been removed (centrifugation, hypotonic lysis, gravity sedimention, density gradient sedimentation, etc.) or the sample may be a plasma enriched with white blood cells by physico-chemical techniques including those mentioned above are preferred.

It is preferred to combine the aqueous dye and blood sample, both as freshly prepared, at the temperature of normal blood or body (about 36°–40° C.) where the analyses planned so indicates. And sharper staining at the higher temperature is generally obtained.

Dye and blood solutions work well when combined volumetrically at a ratio of about 1:4. Gently agitate the mixture for several seconds and examine a drop of the mixture immediately as a wet mount using a glass coverslip under a light microscope or automated differential leukocyte counting device, if available. Other means of contact between the dye and blood cells include using known media, illustratively gelatin, emulsions, etc., impregnated with the dye at about 1% dye concentration. It is quite important, however, not to fix the blood specimen, as is most generally done. Fixing the sample often seriously interferes with the unusual metachromatic action of the dyestuffs of this invention.

Each one of the leukocytes or white blood cells can be identified and distinguished from each other species, class or type by the differential spectral color sorbed, or the different spectral reflection from each of the characteristically dyed species. The examples later included in this specification as illustrative will assist one skilled in the art to appreciate the potential of the novel method proposed. Not the least of the advantages of the method are leukocyte counts (total), leukocyte counts of species, diagnosis of diseases, particularly leukemias, and the monitoring of patients receiving a variety of critical treatments, illustratively, chemotherapy, radiation therapy, ACTH, etc.

It is known that identification and ennumeration of all of the species of leukocytes is critically important in diagnosis and treatment of many diseases.

The examples which follow the detailed description of the invention are intended to illustrate the utility of the invention and its practice. Obviously, they are not exhaustive nor to be considered limiting.

DETAILED DESCRIPTION OF THE INVENTION

This invention provides a single unique pure dye composition and method for distinguishing each species, type or class of the series of leukoytes present in blood from the other including polymorphonuclear leukocytes (neutrophils both mature and immature), eosinophils, basophils, lymphocytes and monocytes by microscopic examination of a single sample of a supravital blood specimen whereby use of standard white light illumination makes possible differentiation, identification, comparison, diagnosis and ennumeration of each of the foregoing species of leukocyte.

At least one supravital blood sample in a fixative free state is brought into intimate contact in an aqueous environment with at least one aqueous basic quaternary cationic organic dyestuff effective to stain one or more of the five foregoing leukocyte species metachromatically at normal body temperature (temperature of normal blood—about 37° C.).

While it is most unusual and very practical that one may elect to use only one of the foregoing pure dyes in any given leukocyte analysis, it is not essential that only one of the pure dyes of this invention be used for the purposes herein as combinations are not thereby excluded. From present experience with basic quaternary cationic dyestuffs, it is submitted as extraordinary to find out of the many examined, none are capable of staining monocytes metachromatically nor staining all of the leukocyte species differentially except those as specifically identified.

Of the first four dyes in Table I, all stain each and every leukocyte species with sufficiently different spectral response within the visible light range to permit identification, differentiation and ennumeration of each of the five species. Three of the foregoing species of dye are identified by their chemical structure sufficiently to establish that they are basic quaternary cationic organic dyestuffs having the unusual metachromatic property noted, that is, the same dye stains each of the leukocytes an individually different spectral color.

It will also be observed in Table I that there are an additional four dyes falling into the same class limitations as provided above. These four dyes, however, have no staining effect upon lymphocytes. However, using any one of these pure dyes in conjunction with blue borrel at about 21°–40° C. will also provide complete differential staining of all leukocytes, as do the first four dyes in Table I.

Blue borrel, in Table I, is most unusual in its ability to stain only lymphocytes at lower temperature (e.g. 21°–25° C.). This makes possible individual studies of this species of white blood cell without further distraction. However, upon working at normal blood temperatures with specimen and dye, all species may be studied at one time using one specimen of blood plus blue borrel dye.

TABLE I

| | METACHROMATIC DYE IDENTITY | SPECTRAL CURVE, IDENTITY AND SOURCE | POLY-MORPHONUCLEAR LEUKOCYTES (NEUTROPHILS) |
|---|---|---|---|
| 1. | GREIFSWALDER'S BLUE 21–40° C. | Spectral Curve #1 no CI no. (Chroma) | YELLOW Granules |
| 2. | BLUE BORREL 21–25° C. | Spectral Curve #2 Michrome #376 | (not stained) |

TABLE I-continued

|  | Dye (Temp) | Source | Neutrophils |
|---|---|---|---|
|  | BLUE BORREL 37-40° C. | (Chroma) | BLUE Granules |
| 3. | RHODANILE BLUE 21-40° C. | Spectral Curve #3 Michrome #1156 E. Merck | MAGENTA Granules RED Cytoplasm |
| 3B. | TOLUYLENE BLUE 21-40° C. | Spectral Curve #11 CI #49410 (Math. Cole & Bell Norwood, Ohio) | BLUE Nucleus YELLOW Granules |
| 4. | NIGHT BLUE 21-40° C. | Spectral Curve #4 CI #44085 (Chroma) | GREEN Granules |
| 5. | PRUNE PURE (GALLO BLUE E) 21-40° C. | Spectral Curve #5 CI #51040 (Chroma | BROWN Granules |
| 6. | HOFMANN'S VIOLET 21-40° C. | Spectral Curve #6 CI #42530 (Chroma) | GREEN Granules |
| 7. | BASIC ORANGE #21 21-40° C. | Spectral Curve #7 CI #48035 (Bayer) | DARK YELLOW Granules (mat) ORANGE Granules (immat) |

|  | EOSINOPHILS | BASOPHILS | LYMPHOCYTES | Orange Granules cytoplasm pink |
|---|---|---|---|---|
| 1. | GREEN Granules | BLUE Granules | BLUE-GREEN Nucleus | PURPLE Nucleus |
| 2. | (not stained) | (not stained) | BLUE-GREEN Nucleus | (not stained) |
|  | PURPLE Granules | RED Granules | BLUE-GREEN Cytoplasm & Nucleus | PURPLE Cytoplasm RED-PINK Granules |
| 3. | PURPLE Granules | RED Granules | BLUE-GREEN Nucleus | LILAC Cytoplasm |
| 3B. | PURPLE Granules | RED Granules | GREEN Nucleus | PURPLE Nucleus PURPLE Cytoplasm |
| 4. | BLUE Granules | PURPLE Granules | (not stained) | PURPLE Nucleus GREEN Cytoplasm |
| 5. | GREEN Granules | PURPLE Granules | (not stained) | PURPLE Nucleus |
| 6. | PURPLE Granules | RED Granules | (not stained) | PURPLE Nucleus RED Granules |
| 7. | BROWN Granules | RED Granules | (not stained) | ORANGE Cytoplasmic Granules |

The first dye of Table I, Greifswalder's blue, is commercially available. However, after extensive searching and some preliminary chemical and physical examination, no reference has been found to identify its chemical structure. As is sometimes the fact in the art of dyestuffs, one positive identification of this very useful dye is by means of its spectral analysis, which is reproduced in its Spectral Curve #1. In Example I, thin layer chromatography has also been relied upon.

It is further noted that the dyes of this invention where the chemical structure is certain are sometimes called or classed as methine or polymethine dyes and sometimes are called carbocyanine dyes. It is presumed that the methine or polymethine name or class may have relation to the bridging structure between the complex aromatic ring structures which contain at least one quaternary nitrogen atom in their ring structures. The chromophoric groups are cationic. Again, we presume these aromatic nitrogen containing ring structures may be the source of the "carbocyanine" nomenclature. U.S. Pat. No. 2,126,852 provides some understanding of one group of methine and polymethine bridged complex basic quaternary cationic dye structures of the carbocyanine designation.

The last dye in Table I herein call basic orange 21 is also unique in that it makes possible for a skilled observer to distinguish spectrally between mature and immature granules of polymorphonuclear leukocytes or neutrophils. Also the clear spectral response identifying monocytes is advantageous in cytological studies as will be touched upon again.

All of the organic dyes within the scope of this inventive method are used in aqueous solution. The strength may be varied to suit the particular conditions of a given study, but it has been found generally feasible to use freshly prepared filtered solutions of the pure dye in distilled water at about 1% dye concentration.

In preparation of the microscopic slides for either visual or automatic differential leukocyte analyses, it is essential to use the prepared blood specimen, free from all fixative additions, and in almost all instances (except as herein noted) preferred to use a temperature of from about 36°-40° C., or body temperature in staining contact. Review of prior art papers has indicated out-standing researchers in blood chemistry have preferred to work in this range.

With the unusual exceptional behavior of blue borrel (see Example 2 and Spectral Curve 2) most advantageous use generally is at about 37° C. All of the dyes, including blue borrel, when used at about 37° C. provide sharper, more intense and spectral differentiation of identifying color spectra with more spectrally acute metachromasia.

However, all the dyes of this invention were originally found effective at ambient room temperature of about 21°–23° C. As mentioned above, at this lower temperature range blue borrel is unique. It then acts only to stain the lymphocytes a blue-green and does not exhibit the exceptional full metachromatic quality as shown in Table I in this cooler temperature range.

Thus, blue borrel is the only known dyestuff among the dyestuffs of this invention that can be used to stain lymphoctes only. Lymphocytes can be exclusively dyed in a fixative-free aqueous environment at, for example 22° C., and only lymphocytes are then differentially developed with a characteristic spectra and can be exclusively studied.

However, as reflected in Table I, at normal blood temperatures the stain-blood sample with blue borrel is universal, by differentially staining and spectrally differentiating each one of the five subject leukocytes, as is also the fact with Greifswalder's blue, rhodanile blue and toluylene blue.

It is to be emphasized that in the method of this invention fixatives are avoided. It is also clear that the term supravital is used as a term of limitation and is intimately associated with the concept of fixative-free blood. To qualify as supravital the sample containing the blood cells are removed or recovered from a living organism, or one freshly sacrificed, or equivalent. The cells should be living cells at the time of their recovery and as near a normal living condition at the time of preparation of the microscopic slide as practicable even as to temperature.

While it is not intended to be bound by theory, it is well known that almost any foreign additive has a tendency to denature proteinaceous materials. Heretofore, use of fixatives in preparation of blood samples for staining has been universal practice. Experience has indicated that fixing interferes with the co-operation between the metachromaticity of the cell and the metachromatic quality of the dyes of this invention. Troublesome artifacts in the field are also thereby avoided.

It is practice to use anti-coagulants in the freshly drawn blood sample, illustratively heparin and E.D.-T.A. However, the least interference with the living nature of the leukocyte cells to be examined after staining, the more accurate the analysis is expected to be.

The leukocyte dyes of this invention metachromatically and supravitally stain a plurality in all cases and all five species of white blood cells when the elected practice prefers this method. Staining is sufficiently instantaneous so that at normal blood temperatures (37° C.) the cytologist does not have to wait or resort to fine cytochemistry before cell dye development occurs and spectral differentiation between the five member family of leukocyte cells before beginning his microscopic studies, either manually or by automated differential leukocyte counting systems.

Illustrative types of fixative free blood samples that can be used:

1. Anticoagulated (E.D.T.A., citrated, heparin) whole blood.
2. Suspensions of leukocyte obtained by dextran and/or gravity sedimentation of anticoagulated whole blood.
3. Samples of whole blood treated with hypotonic solution to lyse red blood cells, leaving primarily white blood cells and platelets behind.
4. Samples of other body fluids, like spinal fluid or pleural or ascitic fluid, as well as samples of joint fluid where white blood cells are of interest.

While the present invention does not specifically provide for an automatic differential leukocyte counting system, such systems have been under in-depth examination.

The College of American Pathologists Conference in Aspen, Colo. August 1975, has published a series of papers delivered at that time in a collection entitled "Differential Leukocyte Counting". These reports provide development and "State of the Art" interest in automatic differential blood cell counting computers. Attention is also directed to U.S. Pat. Nos. 3,916,205 and 4,146,604 (Kleinerman) where certain fluorescent dyes are used in particular combinations for automatic differentiation of certain leukocytes and other blood cells based on fluorescent light response. These references are deemed pertinent to the subject matter and ends of this disclosure. It is to be noted that Kleinenerman relies upon cell fixation, customary in microscopic studies of leukocytes.

The prior art indicates several levels of discrimination in the performance of leukocyte differential counting. Basic or primary is differentiation between polymorphonuclear cells and "mononuclear" cells. On an intermediate level, the differentiation of polymorphs into neutrophils, eosinophils and basophils and the separation of "mononuclears" between monocytes and lymphocytes is said to be possible in principle.

An apparent third level of difficulty involving differentiation of neutrophils into immature and mature forms and the division of lymphocytes into normal and reactive types, controversy has been recognized.

The present state of the art in automated differential leukocyte counters is clearly in the development stage. Manual differentials appear to be principally relied upon. Automated differential counters are said to be of two general classes or groups: 1. pattern recognition systems and 2. cytochemical differentiation systems. It is understood that staining methods of the prior art have been used with greater or less success and machine operators can monitor the operation on a cell-by-cell basis. Usually only 100 cell differential counts are made. Cytochemical systems, while precise, have yet to develop satisfactory calibrators and require highly qualified operators.

In the "LARC" system conventional light microscopy has been used. Inquiry indicates, however, the "LARC" system is no longer available.

As indicated above, the Kleinerman patents disclose compositions, method and apparatus for differential counting and classifying of leukocyte types which comprises distinguishing certain leukocytes, namely; eosinophils, monocytes, lymphocytes, mature and immature neutrophils (but we find no specifics on basophils) by imparting a characteristic fluorescence to all (sic) leukocytes. Light emitted by irradiated fluorescent light is measured and the leukocyte types are classified according to the relative intensities of the emitted light in the characteristic wavelength region of each fluorescent dye. A system is described to provide automated differential counting of the specific leukocytes named.

In a brief survey of the method of the prior art patentee, the following points are of record. 1. At least two light sources are essential including violet and ultraviolet light; 2. A third light source appears needed as well. 3. The system requires a plurality of fluorescent dye stains to identify and differentiate the species of leukocyte. 4. The system requires alcohol-fixed blood smears. 5. Required staining time is of the order of ten minutes and rinsing for one minute followed by drying. 6. There appears to be a decreasing order of fluorescence intensity from (a) eosinophils to (b) neutrophils to (c) monocytes to (d) lymphocytes. (Basophils identification is not reported). 7. In a flow tube system, the blood cells are fixed with formaldehyde and stained with three different dye stains. 8. Detected leukocyte fluorescences are differentially counted and classified by means of ratios of fluorescent light. 9. Patentee's Example 11, indicates identification of only four of the five leukocyte species. 10. Three fluorescent dyestuffs are specified which must be combined to produce a "single dye" composition which combination of dyes appears essential to the operation or method, not merely advantageous.

In the present disclosure, only ordinary white light is essential. No variation in its intensity is required. It is feasible in use of specific ones of the presently disclosed dyestuffs or dye stains herein to employ truly a "single" pure dye. However, it has also been discovered that the pure dyestuffs can also be further used both combined and alone to enhance or augment the spectral differentiation, if required, of each of the five species or individual members of the leukocyte cells which, in the combinations provide considerable advance over the apparent limitations of the Kleinerman multiple fluorescent dye method and provides simple fundamental individual spectral of "white" light identity which will materially assist automated differentiated leukocyte counting apparatus to be more productive and more accurate in identification, differentiation and ennumeration of specific leukocyte cells as well as totals. Also being based on a supravital technique, there is possible a continuous monitoring system in hospital diagnosis and treatment where continuous critical leukocyte observations would be a desired end.

The term supravital stain and supravital staining does not preclude the possibility of continuous perfusion through the blood vessels of living organisms and continuous monitoring of all five species of the white blood cells as they are passed through a specialized tube for observation and count.

It is known that most dyes are toxic when used under supravital conditions. It has been noted that the white cells are easily damaged if all red cells are stained in a warm box at 37° C. Prior art has also noted that if a group of cells are stimulated or damaged, reaction to dyes may be markedly changed. It is not unusual that some dye staining requires relatively long periods, on the order of an half hour to obtain maximum dye intensity. The leukocyte dyes of this invention stain almost instantaneously, no time is required after contact. Thus the cells are subjected to examination in the least denatured form presently known to exist.

Referring specifically to the Drawings and to the Spectral Curves 1 through 10 made a part of this specification, one observes there are two separate curves plotted on the graph by the same instrument. The upper curves, which in general have the lowest peaks and greater frequency of changes in slope, represent ultraviolet light response; while the initially lower curves, having in general fewer and higher peaks, are the visible light response curves.

Positive identification of dye stains by accurate structural chemical information is often known only to the maker, if at all. Even names of dye stains standing alone is not without uncertainty. Systematic nomenclature in the dye art has not been its forte. Introduction of Colour Index numbers is believed reliable identification when known. Other color index systems (Michrome numbers) exist and have been used for further identification where known.

The names as used herein are intended to identify by correspondence the Spectral Curves bearing the color name. Where available, the Colour Index Number and the maker (source) of the dye is recorded. (See Table I). Structural chemical information, where available, has been made a part of the illustrative examples. All dyestuffs used herein were obtained in their purest available form. Study of the spectral response curves indicated, in the main, relatively pure dyestuffs. Where the actual chemical structure is known and of record, there is one predominant, relatively sharp peak in the visible light response curve reflecting the likelihood of and verifying the suspected dye purity.

For purposes of definition in this application, the final arbiter as to identity of names of dyes used shall be the Color Spectra Curves 1 through 11 associated with the said names. These curves are readily and relatively reproducible and are herein relied upon as the "finger print" for ultimate identification of the useful dye stains disclosed and claimed in the presented method of differential cytostaining of the five species of leukocytes, namely; polymorphonuclear leukocytes or neutrophils, eosinophils, basophils, lymphocytes and monocytes; all of which are of interest in the cytology of white blood cells and the diagnosis of various diseases.

The dye stains of Table I are most unusual in that they give spectrally differentiation to the broad class of white blood cells or leukocytes, making possible a cytosorption dye technique for differentiation of the five species of leukocytes. Note that each single dye stain in Table I is not only metachromatic staining of all monocytes but at least four species of white blood cells and provides a different spectral color differentiation for each leukocyte species or class stained.

Referring to the three dyes noted in Table II, it will be observed that they do not possess the intense, broad and unusual multiple metachromatic quality of the dyes of Table I.

TABLE II

| | SPECIFIC DYES | POLYMORPHONUCLEAR LEUKOCYTES (NEUTROPHILS) | EOSINOPHILS | BASOPHILS | LYMPHOCYTES | MONOCYTES |
|---|---|---|---|---|---|---|
| 8. | BASIC RED 13 Spectral Curve 8 (General Analine) | (not stained) | (not stained) | (not stained) | (not stained) | RED Nucleus RED Cytoplasm |

TABLE II-continued

| SPECIFIC DYES | POLYMORPHONUCLEAR LEUKOCYTES (NEUTROPHILS) | EOSINOPHILS | BASOPHILS | LYMPHOCYTES | MONOCYTES |
|---|---|---|---|---|---|
| 9. BASIC VIOLET 16 Spectral Curve 9 (DuPont) | (not stained) | (not stained) | (not stained) | (not stained) | PINK Nucleus PINK Cytoplasm |
| 10. CARBOCYANINE K-5 Spectral Curve 10 (Kodak) | (not stained) | (not stained) | (not stained) | (not stained) | RED Nucleus PINK Cytoplasm |

TABLE III

| COMPOSITION DYES | POLYMORPHONUCLEAR LEUKOCYTES (NEUTROPHILS) | EOSINOPHILS | BASOPHILS | LYMPHOCYTES | MONOCYTES |
|---|---|---|---|---|---|
| 11. CARBOCYANINE K-5 + RHODANILE BLUE (21–40° C.) | BLUE Granules | PURPLE Granules | RED Granules | BLUE-GREEN | REDDISH-BROWN Nucleus REDDISH-BROWN Cytoplasm (more vivid) |
| 12. BASIC VIOLET 16 + BLUE BORREL (37–40° C.) | BLUE Granules | PURPLE Granules | RED Granules | BLUE-GREEN Nucleus | PINK Nucleus PINK-PURPLE Cytoplasm |
| 13. BASIC VIOLET 16 + BASIC ORANGE #21 (37–40° C.) | DARK YELLOW Granules | BROWN Granules | RED Granules | (not stained) | RED Nucleus RED Cytoplasm Granules |
| 14. CARBOCYANINE K-5 + BASIC ORANGE #21 (37–40° C.) | Color as in 7 More intense High contrast | Color as in 7 More intense | Color as in 7 Better Definition | (not stained) | Synergistic 7 and 10 Colors Intensified Excellent |
| 15. NIGHT BLUE + BLUE BORREL (37–40° C.) | GREEN Granules | BLUE Granules | PURPLE Granules | BLUE-GREEN Nucleus | PURPLE Nucleus GREEN Cytoplasm |
| 16. PRUNE PURE + BLUE BORREL (37–40° C.) | BROWN Granules | GREEN Granules | PURPLE Granules | BLUE-GREEN Nucleus | PURPLE Nucleus BRIGHT RED Granules Colors Intensified |
| 17. BASIC ORANGE #21 + BLUE BORREL (37–40° C.) | GREEN Granules | YELLOW Granules | RED Granules | BLUE-GREEN Nucleus | BLUE Cytoplasm |

Although they are metachromatic in a limited or weaker sense, acting on the one species of leukocyte they are of specific and unusual nature in that each is a specific dye for only the one species, monocytes. Because of immediate nuclear staining these cells and not in others these dyes provide a simple, instantaneous and accurate means to identify and differentiate monocytes alone.

In the prior art identification and differentiation of monocytes has been accomplished by time-consuming and complex cytochemical treatment of the cells involving nonesterase reaction, fixed cell preparation, hexazotization, pH adjustment and dye staining with multiple dyestuffs requiring about sixty minutes to accomplish what can be done with any one of these three dyes, alone or in combination, if desired, in less than a minute by a simple dye and blood sample contact in an aqueous system. In the present process as herein disclosed, there is instantaneous preferential staining of the nuclei of monocytes. After dye contact has been made for approximately ten minutes, one can begin to observe the weak metachromasia of the dye in cells other than the monocytes. However, it is delayed, it is not strong, does not confuse, and the monocyte analysis can be completed with good accuracy and reproducibility with the dyes of Table II.

In the research leading to this disclosure, a very large number of the broad spectrum of dye classes were evaluated. The only general class where the chemistry was known found to have any possibility for present purposes were the basic quaternary cationic dyes. Of all the available dyes in this class examined, only those listed in Table I were found to be strongly metachromatic where the differential spectral response to at least four different leukocyte species was rapidly developed. The dyes named in Table II are identified by their Spectral Curves (Spectral Curves 8, 9 and 10). While these three dyes have demonstrated only limited metachromatic synergism with all of the species of leukocytes, the noted specificity of these specific dyes to monocytes is uniquely important.

Identification and ennumeration of monocytes has been simplified by discovery of this set of unusual dyes. The standard fluoride sensitive non-specific esterase reaction cytochemically used for monocyte identification often requires an hour or more to complete and requires accurate cytochemical manipulation to be successful. With any one of the above dyes the dyeing of buffy coat suspension or whole blood and examination can be performed simply, without chemical adjustments, in the order of minutes. Staining of monocytes by the present method is instantaneous as to the nucleus.

In initial use the dyestuffs of Table II immediately identify monocytes by characteristic staining of the nucleus. So far as can be found, no instant staining procedure is presently known which specifically stains the nucleus of monocytes.

The dyestuff of Spectral Curve 10 which is herein called carbocyanine K-5 was the only basic carbocyanine dye in eighteen dyes of this class offered for exploratory use by the manufacturer (Kodak) found to be effective to stain any leukocyte. Progressive intensity of nuclear staining over a short time of exposure suggests unusual affinity of carbocyanine K-5 dye for substances in the nuclei of monocytes.

Identification, differentiation and ennumeration of monocytes has valuable diagnostic significance. Increased numbers of monocytes in the blood may indicate the presence of active tuberculosis, septicemia or blood poisoning and lymphomas like Hodgkins disease in diagnosis. Increased numbers of monocytes in the blood of persons recovering from hypoplastic or aplastic anemia may herald a favorable prognosis for the patient. Rapid and accurate microscopic analyses of monocytes by this method favors extended application of a valuable technique.

Detection, identification and ennumeration of polymorphonuclear leukocytes (neutrophils) are critical parameters in all blood evaluations. They are especially vital in the diagnosis of acute infections like pneumonia or peritonitis where the number of neutrophils are increased. They are important in monitoring patients receiving chemotherapy and for radiation therapy. Decreased numbers can occur in overwhelming infection, as a manifestation of drug toxicity, hyperactivity of the spleen and in acute leukemia.

If the absolute neutrophil count falls below 1000 $mm^3$, the risk of infection increases sharply. The dyes of this invention in general instantly stain the granules or lysosomes which are the characteristic identifying structure of polymorphonuclear leukocytes or neutrophils.

Eosinophils are involved in allergic reactions, as are the basophils. Lymphocytes are involved in inflammation and to a greater extent in immune reactions and response to antigens (foreign bodies).

Eosinophil counts are used in following the medical administration of the adrenocorticotrophic hormone ACTH in the treatment of clinical conditions. Prior methods introduced confusing artifacts and indefinite forms confusingly similar to the eosinophils. Accuracy of the blood cell count with the prior art decreases with the time between blood sample preparation and completion of the count. Multiple dyes are essentially used. Acid and base staining often is required. The dyes used tend to crystallize out of solution on standing.

Lymphocytes, specifically identifiable with blue borrel, are known to be related to inflammation and immunity. They are increased in number in the blood of persons with chronic lymphatic leukemia and in persons with pertussis (whooping cough). The count may be decreased in patients undergoing chemotherapy and radiotherapy, in patients with lymphoma and various types of hereditary immunological deficiencies.

Basophils have a cytoplasm which contains large granules that are rich in cationic substances like heparin, serotonin and histamine. They are involved, for example, in allergic reactions.

The principal advance in the present art has been the discovery that there are very few unique dyes which differentially stain leukocytes, the identity of these few dyes and that they can be used in a single pure form for both manual and automatic identification and study of each species of leukocyte. It is clear that there may be found potential advantages in using combinations of these uniquely useful dyes for cytological purposes. Table III illustrates the result of use of combinations of the specific dyes of Table I and Table II. Use of carbocyanine K-5 and basic orange #21 provides at blood temperature a noticeably improved identification and spectral definition between neutrophils, eosinophils, basophils and monocytes than basic orange #21 alone.

Table III illustrates five combinations of the fundamentally useful and universal dye stains of this invention in combinations, particularly with prune pure and blue borrel, which combination appears to provide synergistic activity in intensifying the spectral definition of individual dyes in the first series of basic quaternary cationic metachromatic dyes for the five members of the leukocytes listed. Members of Table II are also useful for this purpose as illustrated in the combinations of Table III.

The eight dyestuffs set out in Table I and accurately identified by their spectral curves are unusually fully metachromatic. They not only classically stain cells a different spectral color than the dye itself, but all dyes identified in Table I stain each one of the five species of leukocytes spectrally distinguishably different colors in the case of the first four dyes, and each species of the four leukocytes are stained with the second set of four metachromatic dyes of Table I. By some arcane nature, only the lymphocytes remain unstained in the second set of four dyestuffs. Lymphocytes, alone, can be stained with blue borrel at 25° C. for a specific study, which is a very interesting and useful aberration of this specific dye.

Study of the eight dyes in Table I whose chemical identity is known and which exhibit unusual metachromasia when used on fixative free blood samples as herein shown indicates these dyes can be generically classified as basic, metachromatic, cationic dye stains characterized by the presence in the structure of a quaternary nitrogen atom; the anionic portion thereof being a colorless ion, conveniently a halogen ion and most often the chloride ion.

Another definitive quality of the operative dyes of Table I and Table II of this invention is that they are effective within a temperature range of from about 21° to about 40° C. At, or within this temperature range, the spectral difference in their staining quality, when the species of leukocytes are stained, is without altering or changing (otherwise than color) the morphology of the cells. So far as is known, the extent of the synergism between each of the species of leukocyte and the dyes of Table I of this invention in their metachromatic response by combination of the dye with its cellular constituents is utterly unique.

EXAMPLE I (Greifswalder Blue—Spectral Curve #1)

Six patients with typical chronic lymphocytic leukemia donated 50 ml. samples of peripheral venous blood (heparinized). The donors had lymphadenopathy, heptaomegaly, splenomegaly, bone marrows demonstrating virtual replacement by mature appearing lymphocytes, and white blood cell counts from 50,000 to 100,000/$mm^3$.

Ten presumed normal persons donated blood samples, and two patients with viral syndromes who had white blood cell counts from 11,000 to 15,000 mm$^3$ and 70-80% atypical lymphocytes in their peripheral blood. These samples were used for comparison and controls.

In a 10×75 mm. glass test tube containing 5 drops of whole blood, one drop of a freshly prepared filtered aqueous solution of Greifswalder's blue (Chroma) pH 2.1 was added. The mixtures were gently agitated and a drop of the mixture examined immediately as a wet mount under the light microscope and thereafter at 60 second intervals up to 15 minutes subsequent to dye addition to the anticoagulant (heparinized) blood sample. (Not otherwise fixed with any denaturant additions).

In the normal blood samples, Greifswalder's blue stained nuclei and cytoplasm of normal lymphocytes a blue green color. Neutrophils exhibited yellow granules, eosinophils green granules, basophils blue granules and monocytes exhibited purple nucleus. Thus the one dye made possible clear identification of all the normal white cell classes, each with a distinctive identifiable spectral value.

It was also found that the dye-blood sample was stable to heating to the temperature of 37° C. (blood temperature) without changing the characteristic differentiation of the leukocytes present in the samples.

In comparison of the normal blood samples with those of patients with chronic lymphocytic leukemia, it was observed that the dye stained the nuclei and cytoplasm of the leukemic lymphocytes a deep red-brown. In this way, normal lymphocytes can be distinguished from leukemic lymphocytes on the basis of different staining reaction.

It is believed that applications of this technique of cytosorption of vital blood with very select metachromatic dyes which either stain each of the white blood cell leukocytes with identifiably different color spectra or fail to stain one of the class will augment the cytochemistry of blood analysis. Ennumeration of the various cells by both manual and automated differential leukocyte counting and aid positive identification confirmation of disease is augmented.

Greifswalder blue is a most unique dyestuff in that at temperatures including at least those normally of interest in cytochemistry at ambient (25° C.) temperatures to the temperature of blood (37° C.), dye each of the five classes of leukocytes discussed herein is characterized by a different identifiably distinct spectral color. It is unusually and uniquely metachromatic.

Greifswalder blue is listed without a Colour Index Number. The dye is available from Chroma Gesellschaft Schmid & Company, Stutgart, Unterturkheim, Germany. Other biological dye stains of this invention listing (Chroma) as a source may be obtained from the same company.

Thin layer chromatographic analysis of Greifswalder blue confirms that this dye is a mixture of predominantly three basic quaternary cationic dyestuffs. Incomplete data indicates these three dyes are probably Safranin "O" (CI 50240), methylene blue (CI 52015) and methyl violet (CI 42535) or close thereto.

While the evidence indicates Greifswalder blue is not a pure dye, each of the above components is properly classified as a basic quaternary cationic dye. Defining the subject dye in this class is, therefor, orderly.

EXAMPLE 2

(Blue Borrel—Spectral Curve #2)

Heparinized peripheral venous blood samples were obtained at time of diagnosis and prior to treatment from six patients with acute lymphoblastic leukemia, eight patients with acute myeloblastic leukemia, ten patients with acute myelomonocytic leukemia and ten presumed normal volunteers.

In the 24 known diseased cases, routine cytochemical studies were performed. In the case of acute lymphoblastic leukemia, immunological studies indicated one case was B-cell type, 3 cases were T-cell type and two cases were null cell type. The B-cell type case was positive to terminal deoxynucleotidyl transferase. All acute leukemia cases were judged to be typical both morphologically and cytochemically.

Leukocyte rich plasma was obtained from the heparinized samples by sedimentation of the erythrocytes at 4C within sixty (60) minutes.

To five drops of leukocyte rich plasma thereby obtained from each sample in a 10×75 mm. glass test tube were added one drop of a 1% freshly prepared filtered aqueous solution of blue borrel and the tubes were agitated gently for several seconds. At intervals from 1-10 minutes at a temperature of about 21° C., samples of the mixture of cells and dye were removed and microscopically examined as a wet mount. Because of the reputed similarity of methylene blue to blue borrel, a check run was made by adding a 1% aqueous solution of methylene blue dye to separate samples of normal and leukemic leukocytes. All samples were similarly treated and examined. Immersion oil was used as the mounting medium, as fading with "Permount" was priorly noted.

Promptly after dye addition, adherence of small particles of dye was seen in the microscope field along the cell membrane of normal lymphocytes and leukemic lymphoblasts from all patients with acute lymphoblastic leukemia. In all normal and other cytological types of leukemic blasts, adherence of dye to cell membrane did not occur visibly.

In slides demonstrating adherence of dye particles, the cell membrane appeared roughened with small excrescences. Light blue and nucleolar staining appeared after several minutes in these cells, becoming dark blue in about five minutes. At this time, normal lymphocytes and leukemic lymphoblasts appeared degenerated with ragged nucleus and cytoplasm. Dark blue nuclear staining, as found in leukemic lymphoblasts, was not observed in the leukemic monocytes and leukemic myeloblasts. Lymphoid cells were dark blue-green. After ten minutes only a pale yellow nuclear staining and a light green staining of granules was detectable in neutrophils, eosinophils and baseophils. In monocytes blue stained rod-shaped structures (presumed mitochondria) were detectable.

The methylene blue comparison gave faint but observeable nuclear staining in normal lymphocytes and leukemic lymphoblasts but of substantially less definitive spectral intensity than blue borrel.

In a separate test procedure, conducted on similar sedimented normal human blood samples, at a temperature of about 37° C. (blood temperature), a most interesting departure in dyeing of leukocytes was discovered. At this temperature all leukocytes became stained (as had all leukocytes with Griefswalder blue of Example 1 at about 22° C.). Here the neutrophils exhibited blue granules, the eosinophils purple granules, the basophils red granules, lymphocytes blue green cytoplasm and nucleus and monocytes a purple cytoplasm along with red to pink granules.

Thus with blue borrel at lower room temperatures (below about 25° C.) only the lymphocytes had strong spectral dye sorption, but at blood temperature (37° C.), all of the leukocytes were identifiable differentially by singular characteristic spectral dye sorption.

The temperature sensitivity of this unusual basic, quaternary, cationic metachromatic dye stain makes possible clear differentiation of lymphocytes which stain the nucleus of the lymphocytes a blue green at about 21°-25° C.

All the other leukocytes are not stained and such microscopic cytological studies as are deemed warranted can be carried on at the lower temperature. However, at the temperature of normal warm blood (37° C.) all of the remaining leukocytes, namely: neutrophils, eosinophils, basophils and monocytes each are differentiated from the other by use of but one single metachromatic dye.

Mixtures of blue borrel with basic violet 16 tested at 37°-40° C. (Table III) gave little change except all the colors were observed to be slightly more vivid as to the monocytes which also exhibited pink nuclei.

It is likely that computer instrument counting may be made more accurate in machine-optical differentiation with dye blends, and particularly as to monocyte studies. Blue borrel with basic violet 16 for example, (Table III) when used on warm blood (37° C.) indicated all colors of the stained leukocytes were slightly darker and sharper than the blue borrel dye used alone at the same temperature.

Extensive research has not provided the exact structure at blue borrel. However, directions for its manufacture were found in Microtomists Formulary and Guide published by Blaikston & Company, New York, (1956) where one, Peter Gray, discloses manufacture by first preparing an alkaline solution of silver nitrate by adding a 3% aqueous solution of sodium hydroxide to 100 ml. of ½% silver nitrate solution until no further precipitate is produced. The precipitate is washed and clarified by decantation. To the precipitate is added a 1% aqueous solution of methylene blue. Boil five minutes, cool and filter to recover "Borrels' blue".

Thus it is clear that the product dye is a basic quaternary cationic metachromatic dye, which may possibly have a hydroxyl substituted for the original halogen anion, or is possibly complexed with the silver moiety.

The dye is listed as Borrel's Blue Michrome #376 in the latest (Ed.Gurr) E. Merck catalog.

EXAMPLE 3

(Rhodanile Blue—Spectral Curve #3)

Multiple samples of peripheral venous blood was obtained from both normal and leukemic volunteers. Buffy coat leukocytes were obtained therefrom either by centrifugation of 50 ml. heparinized aliquots and removal of the buffy coat layer with resuspension in autologous plasma, or by sedimentation of whole blood containing 5 ml. of 6% dextran in normal saline followed by recovery of leukocytes from the plasma layer. A like series used whole blood.

Volunteers included patients with acute monocytic leukemia, acute myeloblastic leukemia, acute lymphoblastic leukemia, chronic granulocytic leukemia, chronic lymphocytic leukemia and plasma cell leukemia and patients with monocytosis (500/mm$^3$) associated with septicemia.

To samples of normal and leukemic blood containing $6 \times 1.0$ ml. leukocytes per ml., 2 drops of freshly prepared filtered 1% aqueous solution of rhodanile blue (Gurr—see Spectral Curve 3) pH 3.1 was added in a $10 \times 75$ mm. glass test tube. Tubes containing the mixture were agitated for several seconds, and incubated at room temperature for five minutes. At one minute intervals after addition a drop of the mixture was viewed as a wet mount under a clean glass coverslip utilizing conventional light microscopy.

In samples of normal blood and in blood from patients with septicemia and monocytosis, neutrophils contained numerous magenta staining granules that corresponded in size, location and number to granules visualized by conventional panoptic stains. Cytoplasm of neutrophils stained red. Lymphocytes and monocytes contained only several small blue granular appearing and dust-like structures. Eosinophils contained dark violet or purple colored granules, and basophils contained red granules. Nuclei of lymphocytes stained intensely blue green. Pale lilac cytoplasmic staining of monocytes was observed. Nuclei of all peripheral blood leukocytes stained pale green.

In samples of blood from patients with acute myeloblastic leukemia and acute lymphoblastic leukemia, rare small blue granular structures could be seen in the cytoplasm of leukemic blasts. These appeared to be more numerous in the case of leukemic myeloblasts. Staining of the cytoplasm under the conditions of the experiment was not detectable.

In leukemic monocytes from patients with acute monocytic leukemia, blue punctuate appearing structures were found in the cytoplasm of most of the blasts. Within one minute after addition of the dye, blasts from all of the patients with acute monocytic leukemia demonstrated a unique deep rose-pink staining of the cytoplasm. In some instances, this staining assumed a laminar, striated configuration. In other cases, the staining was deep and diffuse. Nucleoli of these and other types of leukemic blasts showed faint violaceous staining.

In blood from patients with chronic granulocytic leukemia, chronic lymphocytic leukemia, and plasma cell leukemia, monocytes did not demonstrate rose-pink cytoplasmic staining. Likewise, leukemic lymphocytes and neoplastic plasma cells did not demonstrate distinctive cytoplasmic staining by rhodanile blue.

Rhodanile blue is an obscure lye formed by the condensation of rhodamine B with Nile blue. (See Spectral Curve 3) Up to this point in time the dye has had limited application in cytochemistry. Studies demonstrate a unique rose-pink metachromatic staining of the cytoplasm of leukemic monocytes of rhodanile blue, a dye that is ordinarily blue in color. This spectral color was not as observed in normal monocytes. Staining of monocytic cells with rhodanile blue appears useful to distinguish both normal monocytes that demonstrate a weak purple or lilac metachromatic staining from leukemic monocytes that demonstrate an intensely positive rose-pink metachromatic reaction. Using a conventional stain for metachromatic substances, these materials could not be demonstrated in studies when applied to fixed cells. Blue punctuate appearing structures in the cytoplasm of leukemic blasts stained vitally with rhodanile blue are interpreted to represent lysosomes and/or mitochondria. Substance(s) in the cytoplasm responsible for the red metachromasia noted with rhodanile blue using living cells are unidentified.

Red metachromasia with rhodanile blue, it is suggested, complements the already existing test for monocytic properties utilizing fluoride sensitive nonspecific esterase. While valuable as a marker for cell of monocytic origin, this cytochemical test is limited in its specificity since many types of cells show nonspecific esterase activity. Sensitivity to fluoride is believed to enhance the specificity of monocytic type nonspecific esterase. As it is formulated presently, the cytochemical test for nonspecific esterase is often difficult to perform, since it depends upon precise adjustments in pH, as well as fresh substrates and complex interactions between dye and couplers.

Compared to the nonspecific esterase reaction for normal and leukemic monocytes, the rhodanile blue metachromatic reaction possesses some advantage. It is advantageous in the identification of leukemic blasts. Selectivity for leukemic monocytes suggests the presence of a unique and as yet unidentified abnormality in these cells compared to normal monocytes. The stain is also advantageous in that it can be applied to living acute leukemia cells that have not been subjected to various forms of fixation as used in conventional cytochemical techniques. This supravital staining technique, it is submitted, minimizes problems with staining and fixation artifact that can occur in specimens treated in the usual way.

The rhodanile blue test is rapid (less than a minute from start to finish) compared to one hour or longer with the usual cytochemical stain for nonspecific esterase. Also, rose-pink metachromasia with rhodanile blue does not require the use of an inhibitor such as sodium fluoride, since as yet, no other type of leukemic blood cell seems to show the rose-pink metachromatic reaction. As experience accumulates, particularly with other types of leukemia including hairy cell leukemia and the leukemic phase of histiocytic lymphoma, the rose-pink metachromatic reaction produced by rhodanile blue promises to be an important addition to the cytochemistry of acute leukemic cells.

Table I indicates normal leukocyte staining with rhodanile blue. Rhodanile blue as the chemical structure shown below:

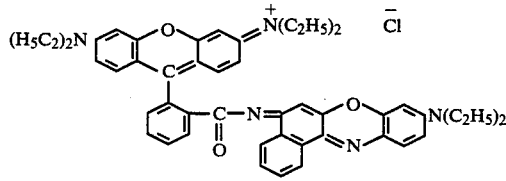

$C_{43}H_{48}N_5O_3Cl$: mol. wt. 780.402

Exact cytotopical diagnosis is essential, because there are now specific treatment for each cytotopic type of acute leukemia. Blue borrel, rhodanile blue and carbocyanine K-5 have all been successfully used in the work here described to distinguish one kind of acute leukemic cell from another.

EXAMPLE 4

(Night Blue—Spectral Curve #3)

Buffy coat leukocytes ($5 \times 10^6$ cells per ml. final concentration) were prepared from 60 ml. heparinized venous blood from each of ten normal volunteers. These were obtained by both centrifugation of 50 ml. heparinized peripheral blood and removal of buffy coat layer and re-suspension in autologous plasma or by sedimentation. In separate experiments whole blood was also used.

One drop of 1% filtered aqueous solution of night blue (Chroma) freshly prepared was incorporated in five drops of blood sample as above described. Mixtures of leukocytes and dye were agitated gently, and a drop of the mixture examined immediately as a wet mount under the light microscope, and at 60 second intervals up to 15 minutes after addition of the dye to the blood sample. Using conventional cytochemical techniques for myeloperoxidase, specific esterase, nonspecific esterase with fluoride an PAS, peripheral blood leukocytes showed typical reactions.

To ascertain lysosomal staining properties of the dye, lysosomes (granules) were separated from granulocytic cells (polymorphonuclear leukocytes, eosinophils, basophils) of 100 ml. peripheral venous blood obtained from each of five presumed normal volunteers by established methods.

Thirty seconds after addition of night blue to a prepared leukocyte suspension of the above blood samples or to the whole blood, granules of polymorphonuclear leukocytes stained yellow brown. Within one minute, granules stained dark green. Nuclei of polymorphonuclear leukocytes appeared to have stained pale green. After one minute, nuclei of lymphocytes appeared unstained (or faintly lavender). Some of the lymphocytes contained green appearing rod shaped structures corresponding in size and shape to mitochondria as visualized with Janus green B. Cytoplasm of lymphocytes appeared unstained.

At one minute, nuclei of monocytes appeared pale lavender, and at two minutes, nuclei of monocytes appeared deep purple. Cytoplasm of monocytes appeared intense green, and contained blue granular appearing structure as well as green fibrillar appearing structures. With fully developed tinctorial properties, monocytes could be readily distinguished from other peripheral blood leukocytes. Within one minute after addition of the dye to cellular preparations, granules of eosinophils stained blue, and granules of basophils stained metachromatically purple. Nuclei of these cells appeared practically unstained (very pale lavender).

Based on limitations inherent in panoptically stained specimens, over the past several decades a number of cytochemical tests have been devised to more precisely distinguish one type of blood cell from another. In general these tests are designed to detect increased amount of one type of substance in a particular cell compared to another, or to detect a substance(s) within a characteristic cellular organelle in one cell compared to another. For example, activity of nonspecific esterase is unusually high in monocytes, and this activity appears to be particularly sensitive to inhibition by sodium fluoride. Likewise, identification of granulocytic cells depend for the most part upon demonstration of properties of lysosomes. For these purposes, detection of myeloperoxidase and specific esterase activities have been useful as cytochemical tests. Lysosomal granules of eosinophils contain myeloperoxidase that is resistant to inhibition by sodium cyanide, and granules of basophils stain metachromatically with a variety of dyes, due in part to their high content of cationic substances like heparin.

As yet, no generally accepted cytochemical test for lymphoid cells has been reported.

In the present studies, rapid supravital staining of peripheral blood leukocytes by night blue is described. Night blue (nachblau) is an obscure basic dye (see structure following the example). It has been used rarely for bio stain purposes. Vital staining of normal human granulocytic cells with night blue rapidly demonstrates that these cells can be distinguished from one another on the basis of tinctorial properties and size of lysosomes, as well as from other blood cells that do not contain these types of lysosomes. Furthermore, virtual lack of staining of lymphocytes by the dye facilitates identification of lymphocytes.

Monocytes show a particularly intense nuclear staining reaction as well as cytoplasmic coloration. Although the dye itself in solution is deep blue, and has a single absorbance peak at 616 nm (see Spectral Curve 4), nuclei of monocytes stain deep purple and cytoplasm of monocytes stains blue green to deep green. The cytoplasm of monocytes contains green staining fibrillar structures easily identified with the vital staining technique. These structures may be analogous to similar laminar-fibrillar structures visualized in ultrastructural studies of human monocytes. Since they are not found in other types of normal human leukocytes, the green fibrillar structures can also be used to distinguish monocytes from other types of leukocytes.

Compared to conventional cytochemical stains for identification of monocytes, neutrophil leukocytes, eosinophils, and basophils, supra-vital staining of peripheral blood leukocytes by night blue has several advantages. It is advantageous because it is rapid, requiring less than two minutes for maximal color development. It is also advantageous because it avoids the use of synthetic substrates and complex azo dyes and couplers as used in conventional cytochemical tests. Prior art cytochemical tests are difficult to interpret because of non-specific precipitation of color reagents, deterioration of substrates and the need for complex adjustments of pH and metallic ion content.

The foregoing supravital stain technique utilizing living blood cells and their differential affinities for supravital staining of these cells with night blue avoids artifacts that often occur with conventional fixatives. We submit that the vital staining technique provided herein defines a more accurate reflection of cellular localization of the dye (eg. lysosomes, fibrillar structures, nuclear chromatin) than presently used conventional stains. With continued experience and improvements in the automated technology of differential blood cell counting, supravital staining of peripheral blood leukocytes with night blue will be an important addition to the cytochemistry of blood and bone marrow cells.

Night blue also known as Basic blue 15, C.I. #44085 has the following chemical structure:

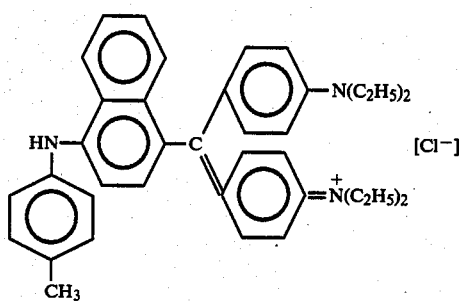

$C_{38}H_{42}N_3Cl$
Molecular weight 576; Cationic weight 541

EXAMPLE 5

Prune Pure—Spectral Curve #5

One drop of a 1% aqueous solution of prune pure dye stain (also known as Gallo blue E) (Spectral Curve 5) made freshly before use was added to five drops of a buffy coat leukocyte suspension ($5 \times 10^6$ ml/final concentration) prepared from 60 ml heparinized venous blood of each of ten normal volunteers. In a separate series of experiments whole venous blood rather than buffy coat was used. The temperature of the blood sample and the dye was held at about 37° C. (body temperature) previous trials having established the dye to be operable from above 21° C. to about 40° C.

After about two minutes, nucleoplasm of monocytes stained intense purple, especially in the areas of heterochromatin. Cytoplasm of the monocytes appeared purple. Nuclei of the lymphocytes stained very faintly lavender (if at all). Polymorphonuclear leukocytes exhibited brown granules, eosinophils green granules and basophils were identified by purple granules. Erythrocytes and platelets did not exhibit visible staining.

Found was an unexpected new use for an obscure stain priorly and primarily used in textile dyeing. Nuclear and cytoplasmic staining is rapid and permits easy distinctions between the four classes of leukocytes which accept the stain and the one remaining member of the white cell group, lymphocytes, which resist the metachromatic staining quality of this basic quaternary cationic dyestuff which has the following structure.

Prune Pure

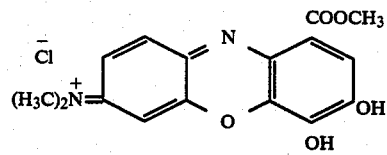

$C_{16}H_{15}N_2O_8Cl$; mol. wt. 350.761

EXAMPLE 6

Hofmann's Violet—Spectral Curve #6

A series of 60 ml heparinized venous blood samples from each of ten normal volunteers was used to prepare one set of $10 \times 75$ mm glass test tube samples containing buffy coat leukocytes and another set containing whole blood (five drops).

An aqueous solution containing 1% of Hofmann's violet, a basic metachromatic quaternary cationic dyestuff having the Colour Index number CI 42530 was prepared. The following structure is believed to represent the true Hofmann's violet. However, the Spectral Curve made a part of this specification is the "finger print" of the dye used in this exploratory work and is the intended arbitor of what is intended by the name as herein used.

Hofmanns violet is a mixture of an alkylated (methyl or ethyl) rosaniline, C.I. 42510; and para rosaniline, C.I. 42500; reacted together with methyl iodide in methyl alcohol.

One drop of the 1% aqueous solution freshly prepared of the basic metachromatic cationic dyestuff represented by Spectral Curve 6 was incorporated in each of the glass test tubes at a temperature of normal blood (37% C.). Drops of the samples were examined as a wet mount under the light microscope at one minute time intervals up to 15 minutes after dye addition to the blood sample.

Monocytes exhibited intense purple staining of nucleus and cytoplasm, and granules were red stained. In two minutes all peripheral blood leukocytes, except the lymphocytes, were spectrally differentiated; the neutrophils reflecting green granules, eosinophils purple granules, basophils red granules, the lymphocytes were essentially not stained and the monocytes were characterized by purple nucleus and red granules. Metachromasia of the dye was strongly exhibited. Use of the foregoing supravital staining technique minimized some of the problems that occur with fixation and use of synthetic substrates as well as complex interactions between products of enzymatic catalysis and unstable azo dyes. Automated differential leukocyte counting instrumentation should become more applicable through the use of normal light microscopy as is made possible by the metachromatic quality of this specific dye, along with the other dyes herein found and illustrated to exhibit extreme metachromasia in differentiation of the foregoing leukocytes.

EXAMPLE 7

Basic Orange #21-Spectral Curve #7)

A series of methine and polymethine dyes, specifically identified chemically, were prepared in 1% concentration in aqueous media. Of the large group, only one was found among those basic quaternary cationic dyestuffs to be metachromatic. This one metachromatic dye stained eosinophil granules (brown), basophils (red) and monocytes (orange cytoplasmic granules) to provide spectrally differentiated members of the group of leukocytes. Quite remarkably, it was also found that the differential staining of both mature and immature neutrophils was more specific than any dyestuff having the metachromatic quality of staining a plurality of leukocytes differentially. It was found that mature neutrophils were spectrally identifiable by dark yellow granules and immature granules could be identified by their orange spectral reflection. Only lymphocytes appeared to remain without stain acceptance or not stained in an identifiable spectra. However, in combination with blue borrel, all five of the specific leukocytes were spectrally identifiable (see Table III).

The polymethine dyestuff is identified as a basic quaternary cationic metachromatic dye having the Spectral Curve as in #7. The dye has been specifically identified as basic orange #21 (also known as Albright orange and Astrazone orange G (200). The chemical structure is reproduced below and it is further identified as CI 48035.

It was found as reported in Table III that combinations of Carbocyanine $K_5$ and basic orange #21 had improved spectral differentiation in distinguishing and identifying for ennumeration in a single blood sample neutrophils, eosinophils, basophils and monocytes. Monocyte definition was considerably sharper and more pronounced than with use of either dye alone indicating synergistic effect.

CI-48035 Basic Orange 21

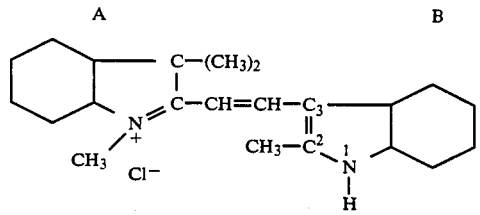

EXAMPLE 8

| Basic Red 13 | and | Basic Violet 16 |
| Spectral Curve 8 | | Spectral Curve 9 |
| CI 48015 | | CI 48013 |

Twenty-two dyes from a commercial source were evaluated. Of these, one was outstandingly metachromatic. It is basic orange 21 (Spectral Curve 7) of Example 7. Two others of this series were found to be very unusual, for they, like carbocyanine K-5 of Example 10 (Spectral Curve 10), specifically stained only monocytes and this staining instantly.

These latter two dyes, as are all the useful dyes of this invention whose structure is known, are basic quaternary cationic organic dyestuffs effective to dye stain leukocytes and in this odd group specifically stain only monocytes. These latter two dyes are identified above.

Ten presumed normal persons donated samples of venous blood. Each sample was drawn in with heparin used as whole blood and prepared as a buffy coat suspension without fixation. Aqueous solutions of about 1% concentration of each of the above pure dyes were freshly prepared in distilled water and filtered. To five drops of the whole blood or the leukocyte rich suspension in two sequential series of blood samples from each of the ten patients was incorporated one drop of basic red 13 dye solution and in the second series the basic violet 16 dye solution was chosen. In the trials in the first and second series (with both of the above dyes) only monocytes were immediately stained. In the case of basic red 13, the nucleus was stained red as well as the cytoplasm. In the basic violet 16 series, the nucleus was more pink and the cytoplasm was also so generally classed as to color. While the colors were spectrally different in appearance, no instrument was available to provide accurate tristimulus values. While the staining of the monocytes was again unique, as with carbocyanine K-5 of Example 10, each of the three dyestuffs gave sufficient color differential in the staining to permit the eye to determine that differences existed. (See Table II).

These three dyes were used also in combinations with the major dyestuffs of Table I as shown in Table III.

It was observed that while a single pure dye (as in Table I) might well provide sufficiently different spectral response to clearly identify each species of leukocyte, some combinations, particularly with the three dyes; carbocyanine K-5, basic red 13 and basic violet 16, offered potential for some observed synergism in dye intensity.

Basic red 13 has the following chemical structure:

BASIC RED 13
CI 48015

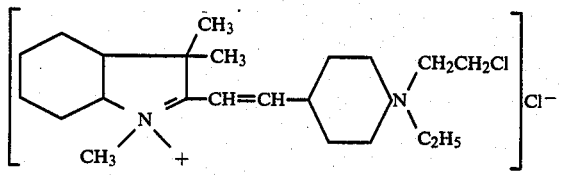

Basic violet 16 has the following chemical structure:

BASIC VIOLET 16
CI 48013

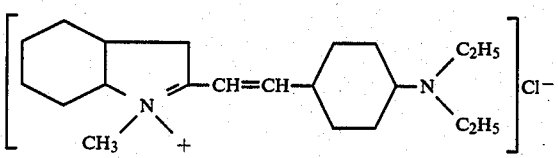

U.S. Pat. No. 2,179,895 of Miller et al., discloses and claims dyestuffs described as being of the methine series including basic red 13. It is also known as Genacyl Pink G, Astrazon Rose FG, Astrazon Pink FG, Basic Rose 2S, Cationic Pink, etc.

Other names given for basic violet #16 are: Astrazon Red Violet 3R, Astraviolet 3R, Sevron brillant red 2-B, etc.

EXAMPLE 9

Toluylene Blue—Spectral Curve #11

Toluylene blue, made by the condensation of m-toluylene diamine with p-nitroso-dimethylaniline hydrochloride was prepared in 1% aqueous solution and filtered as in the prior examples.

Venous blood from each of ten normal volunteers was identified in two series of blood samples, as in previous examples. One series was prepared into buffy coat leukocyte suspensions. A second series was carried forward as whole venous blood. The samples were kept in a warm box at about 37° C.

One drop of the dye solution was incorporated into each of the samples in the order of their observation. In each of the cases as above indicated, the dye containing sample was subjected to observation under light microscopy as is the general procedure in manual observation of leukocytes. In each case within about five minutes of incorporation of the aqueous dye and the prepared blood sample free from all fixatives such as methyl alcohol, formalin, etc., the neutrophils developed blue nucleus and yellow granules, eosinophils were distinguished by purple granules, basophils developed red granules, lymphocytes green nucleus and monocytes developed purple nucleus and purple cytoplasm. Each of the species of white blood cells were spectrally differentiated from one another by the use of a single pure metachromatic dye characterized by its cationic nature, quaternary nitrogen atom and halogen anion. While it has been heretofore recognized that certain dyes will stain biological specimens a different color than the dye (metachromasia), it has not been reported that a basic single pure dye without external adjustments of pH and other preparation can be used to stain leukocytes at body temperature in an aqueous environment and without fixation to identify by spectral differences each of the five individual leukocyte species.

Toluylene blue has the general structural formula:

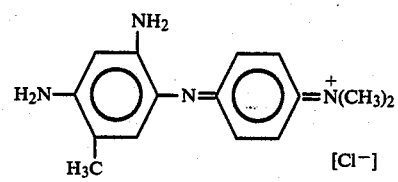

$C_{15}H_{19}N_4Cl$
Molecular weight 291: Cationic weight 256

EXAMPLE 10

$(1,1^1$—diethyl—$2, 2^1$ cyanine bromide) Spectral Curve #10

Eighteen carbocyanine dyes having the chemical structures and graded redox potentials as were listed in Science, Apr. 30th and Scientific American in May of 1974 (Kodak advertisement) were evaluated for potential advantage in studies of vital leukemic blood.

PART I

In duplicate test series, samples of leukocyte rich plasma and whole blood from normal persons and from patients with acute leukemia were subject to staining with the entire series of the above 18 dyes of graduated redox potential. One drop of a 1% aqueous solution of the pure dye was intermixed by gentle agitation with five drops of the leukocyte containing heparinized blood samples.

Only the above $1, 1^1$—diethyl—$2, 2^1$ cyanine bromide (herein called carbocyanine K-5) gave instant strong spectral sorption or staining of leukocytes and then specifically with monocytes. Progressive nuclear red staining continued to develop over half an hour. The rationale for the peculiar selectivity of this dye for the nuclei of monocytes uniquely has not been fully understood. It is, however, a basic quaternary cationic dyestuff having a unique quality.

PART II

Supravital blood samples of the following normal persons and patients who had untreated leukemias were subjected to staining with carbocyanine K-5. Blood samples both of gravity sedimented leukocyte rich plasma and venous whole blood were subjected to staining. No significant differences were noted when comparing samples of whole blood to samples of leukocyte-rich plasma in the test series.

20 normal persons
8 persons—acute lymphoblastic leukemia
6 persons—acute myeloblastic leukemia
10 persons—acute monocytic leukemia In all instances the above blood samples were subjected to prior art routine cytochemical stains including specific esterase, non specific esterase with fluoride inhibition, PAS (periodic acid-Schiff) and myeloperoxidase were used to confirm the morphologic assessment of these leukemic specimens. All cases were observed as typical both morphologically and cytochemically.

One drop (1% in aqueous solution) of the selected cyanine dye was added to five drops of whole blood in a 10×75 mm. glass test tube of the vital blood sample. Cell concentration was controlled to about $5 \times 10^6$ cells per ml. The pH was 6.2. Through current cytochemical tests for distinguishing between cell types, these cells were established to consist of (1) polymor phonuclear leukocytes, (2) lymphocytes, (3) eosinophils, (4) basophils and (B 5) monocytes as determined through Wrights staining as well.

Approximately one minute after addition of the dye to samples of normal blood, 5 to 20 orange rod-shaped structures were detected in the cytoplasm of monocytes and lymphocytes. Over the next several minutes, the nucleus of the normal and leukemic monocytes stained first a pale pink. Within 10 minutes the nucleus developed to a deep pink and finally a bright orange-red with some apparent luminescence (incandescent light). Under Zeiss fluorescent microscope, nuclei and cytoplasm of normal monocytes exhibited red fluorescence.

Nuclei of other normal peripheral blood leukocytes stained faintly, if at all. Granules of other leucocytes; polymorphonuclear eosinophils and basophils stained a faintly discernable pale yellow to greenish yellow. Erythrocytes did not exhibit visible staining.

Blood samples from patients with acute lymphoblastic leukemia showed only mitochondrial staining as did the leukemic myeloblasts from patients with myeloblastic leukemia. Patients with acute monocytic leukemia, however, exhibited intense red-orange nuclear staining and red nuclear fluorescence after 5-10 minutes as did the normal monocytes.

Observations as above and others demonstrate conclusive and unusual characteristic affinity of this one specific carbocyanine dye for nuclear substances of monocytes.

From analysis by human observations, it is also apparent that automated differential cell counters may be made more useful and extended in scope to use advantageously the foregoing dye-stain technique to differentiate, enumerate and classify different leukocytes, and particularly as here, monocytes, by a single aqueous dye contact with a supravital blood sample without prior fixation and denaturation to introduce artifacts.

Further experimental use of carbocyanine K-5 in combinations with metachromatic dye stains of this invention indicated most unusual results in 1:1 combination with basic orange #21 (Spectral Curve #7). In use of the foregoing combination the stained white blood cell leukocytes in every instance were sharper, more intense with better spectral differentiation than with basic orange #21 alone but with much the same visual color. Only lymphocytes were not stained. This dye blend provides an excellent combination for clear differentiation and ennumeration of neutrophils, eosinphils, basophils and monocytes.

Carbocyanine K-5 was also used in combination with rhodanile blue. The advantage was marked and observable but of less synnergistic quality than that found with the basic orange #21-carbocyanine K-5 combination. (see Table III)

The chemical structure of carbocyanine K-5 is reproduced below. The chlorine group can be any halogen.

Carbocyanine K-5

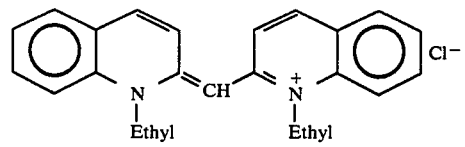

DEVELOPMENT OF THE INVENTION

In the foregoing specification and examples there has been some emphasis on the importance of the advances here disclosed in application to automated differential leukocyte computing devices. There is no known "off the shelf" equipment capable presently without some modification of taking advantage of the method herein disclosed which has been employed manually. Those skilled in the art and working in the field of medical technology are aware of the importance of rapid, accurate determination of the various differential leukocyte counts for a variety of ends. It has been estimated that in the United States each day an half million differential leukocyte counts are performed, most of them by manual techniques at an annual cost of over 750 million dollars.

Such counts, whether manual or automated, have a fundamental requirement of identification, spectral differentiation, ennumeration and diagnostic aid in practice of medicine. The foregoing advance in these fundamentals will no doubt give rise to advances in ancillary automated equipment as herein indicated.

Blood counts as are of concern herein, whether manual or automated, are vital aids in examination and determination of the nature of disease. Fevers of unexplained origin; whether viral or non-pyogenic infection, pyogenic involving appendix, gall-bladder, fallopian tubes; prognosis of patients with various diseases in various stages; malignancies including Hodgkins disease; pulmonary disease; surveillance of patient treatment with adrenocortical steroids; various kinds of acute and chronic leukemias; differentiation in diagnosis between aseptic infarction of bone and osteomyelitis; bacterial infections and many other medical questions are aided in diagnosis, prognosis and treatment by accurate leukocyte counting, analysis and cytological study.

Clinical interpretations and conclusions drawn from stained leukocyte cells whether from venous blood, bone marrow, urine or other sources of vital blood, including occult blood specimens may be employed using the methods inherent in the foregoing exposition.

As used herein, the term metachromatic has relation to not only to the peculiar and unusual quality of the dyestuffs disclosed but to the quality of the various components, illustratively nucleus and cytoplasm, of each of the individual species of leukocytes which metachromatically coreact with something akin to synergism to produce the differentiation in spectral response which makes the described advances in cytochemistry possible. In essence, each white blood cell species sorbs (or fails to sorb) a single metachromatic dyestuff in some unusual and unique manner so that each dye-sorbed cell reflects an individual and different light spectra.

Having thus described the best mode presently known to practice the disclosed invention, what is claimed is:

1. A dye sorbed and metachromatically dye stained, supra-vital, human blood cell specimen wherein minimally the monocytes species of leukocytes present in said dye sorbed specimen are differentiated, identified and enumerated by said dye sorption of color from among all other leukocytes present in said dye-sorbed specimen; said other leukocyte species comprising neutrophils, eosinophils, basophils and lymphocytes, said dye selected from the group of metachromatic dyes consisting of Griefswalder's Blue, Blue Borrel, Rhodanile Blue, Toluylene Blue, Night Blue, Prune Pure, Hofmann's Violet, Basic Orange 21, Basic Red 13, Basic Violet 16 and Carbocyanine K-5 and their admixtures; said monocytes therein identified by the dye sorbed metachromatic differentiating color of their component nucleus and cytoplasm.

2. A composition of matter which comprises:
   (a) A leukocyte cell containing human blood specimen in a supra-vital fixative-free, aqueous environment reacted with
   (b) At least one pure, organic, basic quaternary cationic dyestuff; said dyestuff differentiated from all other dyes in said class by the fact that in said foregoing composed environment all monocytes are stained metachromatically and differentially from all other blood cell leukocytes present in said dye stained composition.

3. The composition of claim 2 wherein the quaternary cationic dyestuff is selected from the group consisting of Griefswalders' blue, blue borrel, rhodanile blue, toluylene blue, night blue, prune pure and Hofmann's violet.

4. The composition of claim 2 wherein the quaternary cationic dyestuff is selected from the group consisting of basic red #13, basic violet #16, carbocyanine K-5 and basic orange #21.

5. The composition of claim 2 wherein the quaternary cationic dyestuff is basic orange #21.

6. In a dye staining method for differential analysis of at least one of the leukocytes species consisting of neutrophils, eosinophils, basophils, lymphocytes and monocytes present in a human blood specimen; the improvement which comprises staining a supra-vital, aqueous human blood cell containing specimen within a temperature range of 21 to 40 C. with at least one substantially chemically pure, organic basic quaternary cationic dye; all of the said dyes useful within said class characterized by their unique and unusual quality of differentially and metachromatically staining, minimally, the monocytes in said leukocyte group; thereafter and thereby enabling the minimal identification, differentiation and enumeration of the said monocytes among said other leukocyte species in said blood specimen under white light absorbance means.

7. The method of claim 6, wherein a single blood sample is subjected to aqueous staining contact with at least one aqueous basic quaternary metachromatic cationic organic dyestuff effective to dye stain the individual leukocytes present in the sample metachromatically at blood temperature, said stained cells subjected to differentiation and ennumeration; differentiation by selection of a color sensitive filtering element having a settable spectrum range sensitive to the spectrum reflected from each of the differentially stained white blood cells in said sample, and reflected light stimulus activated counting means, thereby differentially counting the number of each of the individual species of leukocytes present in the sample examined under and within a predetermined field.

8. The method of claim 6, wherein the useful metachromatic dyestuff is selected from the group consisting of basic red #13, basic violet #16, carbocyanine K-5 and basic orange #21.

9. The method of claim 6 wherein the useful metachromatic dyestuff selected is blue borrel.

10. In the method of claim 6, the specific step of differentiating and enumerating the lymphocyte species of leukocytes from other members of the leukocyte class which comprises using blue borrel as the sole cationic metachromatic dye present and controlling the temperature of the composition below about 37° C. but not less than about 21° C. during composing of the composition and completion of such qualitative and quantitative determinations on the so individually stained lymphocytes as are required.

11. The method of claim 6 wherein the said analytical method is performed under physical white light absorbance spectra responsive instrumented automatic differential counting means.

12. The method of claim 6 wherein the defined analytical method is performed by human observation under white light absorbant microscopic examination means.

13. The method of claim 6 wherein at least one substantially chemically pure organic basic quaternary cationic metachromatic dyestuff is selected from the group consisting of Griefswalders' blue, blue borrel, rhodanile blue, toluylene blue, night blue, prune pure and Hofmann's violet.

14. The method of claim 8 wherein the one useful metachromatic dyestuff is basic orange #21.

15. The method of claim 6, wherein at least one of the useful metachromatic dyestuffs is selected from the group consisting of Griefswalders' blue, blue borrel, rhodanile blue, toluylene blue, night blue, prune pure and Hofmann's violet and at least one other of the useful metachromatic dyestuffs present in the said method is selected from the group consisting of basic red #13, basic violet #16, carbocyanine K-5 and basic orange #21.

16. A qualitative and quantative method of blood analysis for differential determination of blood leukocytes present in a supra-vital human blood specimen the steps which comprise:
   (a) Composing said blood specimen in a fixative free aqueous environment with
   (b) At least one organic basic quaternary cationic dyestuff; said class of dyes identified by and restricted to those dyes in said class which stain monocytes metachromatically and differentially from all other leukocytes, said blood leukocytes consisting of neutrophils, eosinophils, basophils, lymphocytes and monocytes; thereby inherently forming a differential dye-stained leukocyte cell-containing composition; said composition uniquely useful thereafter in providing means to differentiate, identify and enumerate the so dyed individual leukocyte species present therein from all other leukocyte cells present in said metachromatically dyed cell differentiated blood cell containing composition by both automatic and manual cell differentiating means.

* * * * *